United States Patent
Bogue

(10) Patent No.: US 8,577,488 B2
(45) Date of Patent: Nov. 5, 2013

(54) METHOD AND SYSTEM FOR OPTIMIZING FILM PRODUCTION AND MINIMIZING FILM SCRAP

(75) Inventor: Beuford A. Bogue, New Carlisle, IN (US)

(73) Assignee: MonoSol Rx, LLC, Warren, NJ (US)

( * ) Notice: Subject to any disclaimer, the term of this patent is extended or adjusted under 35 U.S.C. 154(b) by 625 days.

(21) Appl. No.: 12/753,152

(22) Filed: Apr. 2, 2010

(65) Prior Publication Data

US 2011/0196525 A1   Aug. 11, 2011

Related U.S. Application Data

(60) Provisional application No. 61/303,409, filed on Feb. 11, 2010.

(51) Int. Cl.
| | |
|---|---|
| G06F 19/00 | (2011.01) |
| G21F 9/00 | (2006.01) |
| B09B 3/00 | (2006.01) |
| E02D 31/00 | (2006.01) |
| C02F 1/00 | (2006.01) |
| D06N 7/00 | (2006.01) |

(52) U.S. Cl.
USPC ............ 700/103; 588/14; 588/255; 588/256; 588/260; 588/261; 428/147

(58) Field of Classification Search
USPC ............ 588/14, 255, 256, 260, 261; 428/147; 700/103
See application file for complete search history.

(56) References Cited

U.S. PATENT DOCUMENTS

| | | | | |
|---|---|---|---|---|
| 3,610,415 A | * | 10/1971 | Deak | 209/466 |
| 3,721,346 A | * | 3/1973 | Lore et al. | 210/121 |
| 3,893,656 A | * | 7/1975 | Opacic et al. | 366/106 |
| 3,912,577 A | * | 10/1975 | Akune et al. | 588/320 |
| 3,953,961 A | * | 5/1976 | Harrap et al. | 57/301 |
| 3,973,735 A | * | 8/1976 | Ito et al. | 241/73 |
| 4,042,497 A | * | 8/1977 | Maltby | 210/744 |
| 4,092,095 A | * | 5/1978 | Straitz, III | 431/114 |
| 4,179,263 A | * | 12/1979 | Jung et al. | 588/321 |

(Continued)

FOREIGN PATENT DOCUMENTS

| | | |
|---|---|---|
| CN | 1812773 A | 8/2006 |
| CN | 1914618 A | 2/2007 |
| WO | 97/26607 A1 | 7/1997 |
| WO | 2006/031209 A1 | 3/2006 |

OTHER PUBLICATIONS

Mehrabzadeh et al., "Recyling of Commingled Plastic Waste Containing Polypropylene, Polyethylene, and Paper", Iran Polymer Institute, 2000, 5 pages.*

(Continued)

Primary Examiner — Kavita Padmanabhan
Assistant Examiner — Thomas Stevens
(74) Attorney, Agent, or Firm — Hoffmann & Baron, LLP

(57) ABSTRACT

The present invention relates to a method of optimizing self-supporting film production. The method includes the steps of: determining at least one scrap factor which relates to a total amount of scrap in processing a film product; correlating the at least one scrap factor to at least one processing parameter; and adjusting the at least one processing parameter to reduce the total amount of scrap in processing the film product. The present invention also relates to a system for optimizing film production.

23 Claims, 14 Drawing Sheets

(56) References Cited

U.S. PATENT DOCUMENTS

| | | | | |
|---|---|---|---|---|
| 4,287,147 | A | * | 9/1981 | Hungerford .................. 264/146 |
| 4,288,038 | A | * | 9/1981 | Williams ......................... 241/52 |
| 4,353,967 | A | * | 10/1982 | Hungerford .................. 428/520 |
| 4,409,137 | A | * | 10/1983 | Mergan et al. ..................... 588/3 |
| 4,509,434 | A | * | 4/1985 | Boday et al. .................. 110/238 |
| 4,590,149 | A | * | 5/1986 | Nakane et al. ................ 430/325 |
| 4,716,802 | A | | 1/1988 | O'Connor et al. |
| 5,064,466 | A | * | 11/1991 | Hilton ............................. 75/417 |
| 5,193,936 | A | * | 3/1993 | Pal et al. .................. 405/128.75 |
| 5,207,176 | A | * | 5/1993 | Morhard et al. ............. 110/246 |
| 5,266,494 | A | * | 11/1993 | Lahoda et al. .................. 436/57 |
| 5,318,383 | A | * | 6/1994 | Yates et al. ................ 405/129.2 |
| 5,401,444 | A | * | 3/1995 | Spinello ........................ 264/0.5 |
| 5,489,737 | A | * | 2/1996 | Baba et al. ........................ 588/2 |
| 5,496,392 | A | * | 3/1996 | Sims et al. ..................... 75/414 |
| 5,732,364 | A | * | 3/1998 | Kalb et al. ........................ 588/8 |
| 5,815,398 | A | | 9/1998 | Dighe et al. |
| 5,853,474 | A | * | 12/1998 | Hilton ........................... 106/697 |
| 7,096,161 | B2 | * | 8/2006 | Smith et al. ................... 702/188 |
| 8,282,892 | B2 | * | 10/2012 | Sampson ...................... 422/295 |
| 2004/0102867 | A1 | | 5/2004 | Palanisamy et al. |
| 2004/0255484 | A1 | * | 12/2004 | Storrer et al. ..................... 34/92 |
| 2005/0055123 | A1 | | 3/2005 | Franz |
| 2005/0222781 | A1 | | 10/2005 | Yue et al. |
| 2008/0260805 | A1 | | 10/2008 | Yang et al. |
| 2009/0003509 | A1 | * | 1/2009 | Hosokawa et al. ........... 376/310 |
| 2009/0135344 | A1 | * | 5/2009 | Suzuki et al. ................... 349/96 |
| 2010/0249486 | A1 | * | 9/2010 | Bar Nathan et al. .......... 588/309 |
| 2011/0020600 | A1 | * | 1/2011 | Sasata et al. .................. 428/141 |

OTHER PUBLICATIONS

Ching et al., "Plastic Recycling in Business Machines', Reuse and Recovery Assessment" IBM Corporation, IEEE, 1996, 189-193.*
Colvin-R., "Cast Film Systems are Ready for Inline Inspection" Modern Plastics, Oct. 2001, version 78,3 pages.*
Kadykowski-R., "1984 Polymers,Laminations and Coatins Conference; Reclaim Systems for Film Processing", 1984, 9 pages.*
Notification of Transmittal of the International Search Report and the Written Opinion of the International Searching Authority, or the Declaration for International Application No. PCT/US11/24340 dated Apr. 7, 2011, 4 pages.
Written Opinion of the International Searching Authority for International Application No. PCT/US11/24340 dated Apr. 7, 2011, 4 pages.

* cited by examiner

METHOD AND SYSTEM FOR OPTIMIZING FILM PRODUCTION AND MINIMIZING FILM SCRAP

CROSS-REFERENCE TO RELATED APPLICATIONS

The present invention claims priority to U.S. Provisional Application No. 61/303,409, filed Feb. 11, 2010, the contents of which are incorporated by reference herein.

FIELD OF THE INVENTION

The present invention relates to maximizing the efficiency and minimizing the cost of producing film that is dosed with agents and medicaments. Specifically, the present invention relates to a process and system for minimizing the waste of materials in the processing of film doses.

BACKGROUND OF THE INVENTION

When film dosages are manufactured, especially self-supporting film dosages, the film is generally formed into individual doses. There is often scrap, either in liquid, mixed form or in solid form, associated with the manufacturing and processing steps. This scrap results in unusable and therefore wasted material. When such wasted material includes precious material such as active drugs and pharmaceuticals, this wasted material can be extremely expensive. Current processes and manufacturing designs employ systems that result in scrap in liquid and/or solid form. Thus, the current processes and manufacturing designs are inefficient and ultimately may cost a higher amount to make individual dosage forms.

It is desirable to solve the present problems associated with the art to yield a more efficient manufacturing process to form individual film doses, especially those containing an active component.

SUMMARY OF THE INVENTION

An aspect of the present invention includes a method of optimizing self-supporting film production which includes the steps of: determining at least one scrap factor which relates to a total amount of scrap in processing a self-supporting film product; correlating the at least one scrap factor to at least one processing parameter; and adjusting the at least one processing parameter to reduce the total amount of scrap in processing the film product.

Another aspect of the present invention includes a system for optimizing self-supporting film production which includes: a self-supporting film manufacturing apparatus; including a mixer, a film former, and a slitter; a processor for compiling and processing data related to the self-supporting film manufacturing system, and at least one process characteristic; wherein the processor remotely controls at least one parameter to optimize a yield of self-supporting film dosage product.

The various aspects of the present invention include utilizing a computer system in conjunction with the film manufacturing and processing equipment and apparatus in order to determine one or more scrap factors, correlate a scrap factor to at least one processing parameter, and adjust the processing parameter, where the adjusting step may be prior to initializing the production process, in-line with production, between runs, or during various predetermined points in the process. As such, it is possible to reduce the amount of scrap produced in the manufacturing of the self-supporting film product, thereby increasing efficiency in manufacturing as well as yield.

The present invention with its various embodiments may be better understood through a study of the following figures and description.

DETAILED DESCRIPTION OF THE DRAWINGS

Figure 1:
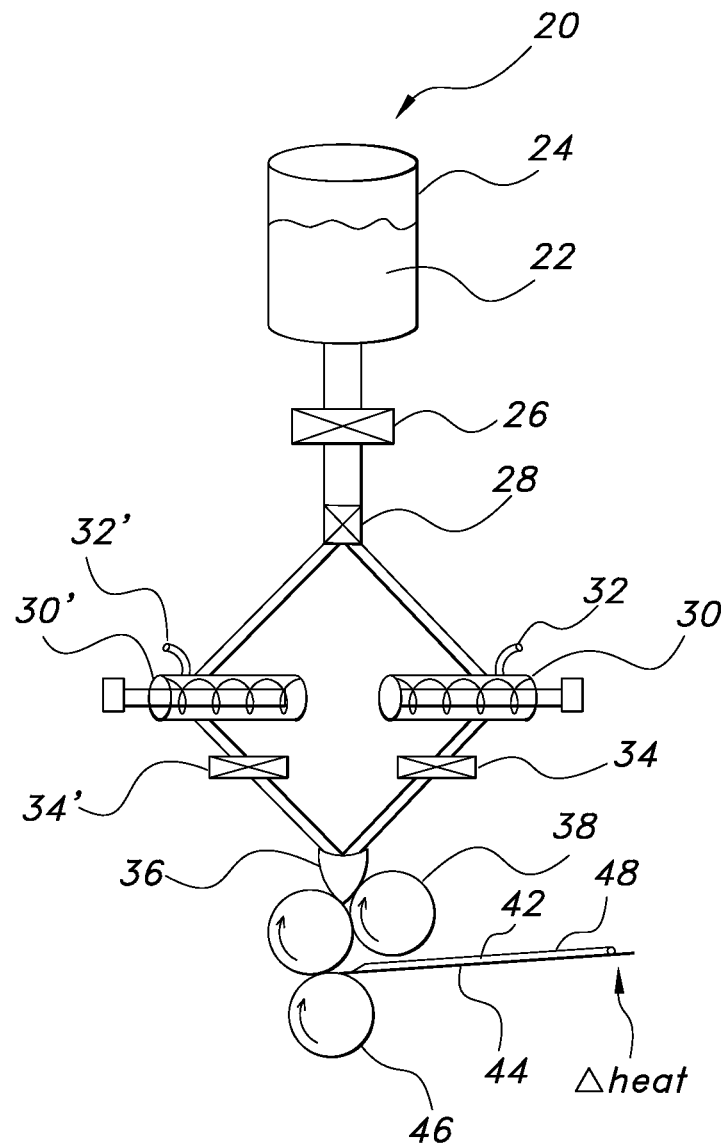
FIG. 1 is a schematic view of an apparatus suitable for preparation of a pre-mix, addition of an active, and subsequent formation of the film.

Film systems embody a field of technology that has major advantages in areas of administering drug, medicament, and various other active and agent delivery systems to an individual in need thereof. In order to provide a desirable final product which exhibits advantageous characteristics and desirable properties, the processing and manufacturing of film strips and film technology is technologically demanding and cumbersome.

As used herein, the terms "pharmaceutical", "medicament", "drug" and "active agent" may be used interchangeably, and refer to a substance or composition useful for the prevention or treatment of a condition. The terms may include pharmaceuticals, neutraceuticals, cosmetic agents, biologic agents, bioeffective substances, and the like.

It will be understood that the term "film" includes delivery systems of any thickness, including films, sheets, discs, wafers, and the like, in any shape, including rectangular, square, or other desired shape. The film may be in the form of a continuous roll of film or may be sized to a desired length and width. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution of components through the application of controlled drying of the film. Films may include a pouch or region of medicament between two films.

In some embodiments of the invention, the films are intended for oral administration. In other embodiments, the films are intended for topical administration. As used herein, the term "topical agent" is meant to encompass active agents that are applied to a particular surface area. For example, in one embodiment, a topical agent is applied to an area of the skin. In other embodiments, the topical agent may also be applied to mucosal areas of the body, such as the oral (e.g., buccal, sublingual, tongue), vaginal, ocular and anal areas of the body. In other embodiments, a topical agent is applied to a hard surface, such as a particular surface area in need of treatment.

The medicament may be dispersed throughout the film, or it may be deposited onto one or more surfaces of the film. In either way, the amount of medicament per unit area is desirably uniform throughout the film. It is desired that the films of the present invention include a uniformity of component distribution throughout the volume of a given film. Such uniformity includes a substantially uniform amount of medicament per unit volume of the film, whether the medicament is within the matrix of the film or coated, laminated, or stabilized on one or more surfaces thereof When such films are cut into individual units, the amount of the agent in the unit can be known with a great deal of accuracy.

Uniformity of medicament throughout the film is important in administering an accurate and effective dose of medicament to a user. Various methods of forming uniform films, as well as various additives and fillers, may be used, including those methods and materials described in U.S. Pat. Nos. 7,425,292 and 7,357,891 and U.S. Publication No. 2005/0037055, which are herein incorporated by reference in their entireties.

Some constituents of the film strip are very expensive, and thus are desirably used sparingly. For example, active agents may be extremely expensive, and thus waste of such materials is preferably limited. A wide variety of medicaments, bioactive active substances and pharmaceutical compositions may be included in the dosage forms of the present invention. Such medicaments, bioactive substances and pharmaceutical compositions may be useful as topically-administered dosages or as orally-ingestible dosages.

Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, uterine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin IB®, Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP® and Aminofen®), and combinations thereof that may optionally include caffeine. Other pain relieving agents may be used in the present invention, including meperidine hydrochloride (commercially available as Demerol®), hydromorphone hydrochloride (commercially available as Dilaudid®), propoxyphene napsylate and acetaminophen (commercially available as Darvocet-N®), Fentanyl (commercially available as Duragesic® and Fentora®), sodium hyaluronate (commercially available as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The present invention may further include agents such as NSAIDs, including etodolac (commercially available as Lodine®), ketorolac tromethamine (commercially available as Acular®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), and misoprostol (commercially available as Cytotec®). Opiate agonists and antagonists, such as buprenorphine and naloxone are further examples of drugs for use in the present invention.

Other preferred drugs for other preferred active ingredients for use in the present invention include anti-diarrheals such as loperamide (commercially available as Imodium AD®, Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other active agents useful in the present invention include, but are not limited to alcohol dependence treatment, such as acamprosate calcium (commercially available as Campral®); Allergy treatment medications, such as promethazine hydrochloride (commercially available as Phenergan®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenydramine HCL (available as TheraFlu®) and clemastine (available as Tavist®).

Films of the present invention may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), and memantine (commercially available as Namenda®); anemia medication, such as cyanocobalamin (commercially available as Nascobal®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and $Ca^H$-antagonists such as nifedipine (commercially available as Procardia® and Adalat®).

Actives useful in the present invention may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

The present invention may further include one or more Antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), and anastrozole (commercially available as Arimidex®); anti-coagulants, such as aspirin with extended-release dipyridamole (commercially available as Aggrenox®), warfarin sodium (commercially available as Coumadin®), dipyridamole (commercially available as Persantine®), dalteparin (commercially available as Fragmin®), danaparoid (commercially available as Orgaran®), enoxaparin (commercially available as Lovenox®), heparin (commercially available as Hep-Lock, Hep-Pak, Hep-Pak CVC, Heparin Lock Flush), tinzaparin (commercially available as Innohep®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan®), darifenacin (commercially available as Enablex®), and solifenacin succinate (commercially available as VESIcare®); blood vessel constrictors, such as methylergonovine maleate (commercially available as Methergine®); cholesterol lowering medication, including paricalcitol (commercially available as Altocor®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus met®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), and tolazamide (commercially available as Tolinase®).

Other useful agents of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®). bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Agents useful herein may also include treatment for emphysema, such as tiotropium bromide (commercially available as Spiriva®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide(commercially available as Zonegran®), levetiracetam (commercially available as Keppra®), and phenytoin sodium (commercially available as Dilantin®).

Erectile dysfunction therapies useful herein include, but are not limited to, drugs for facilitating blood flow to the penis, and for effecting autonomic nervous activities, such as increasing parasympathetic (cholinergic) and decreasing sympathetic (adrenersic) activities. Useful agents for treatment of erectile dysfunction include, for example, those agents available as alprostadil (commercially available as Caverject®), tadalafil (commercially available as Cialis®), vardenafil (commercially available as Levitra®), apomorphine (commercially available as Uprima®), yohimbine hydrochloride (commercially available as Aphrodyne®, Yocon®), and sildenafil citrate (commercially available as Viagra®).

Agents useful herein may further include eye medications and treatment, such as dipivefrin hydrochloride (commercially available as Propine®), valganciclovir (commercially available as Valcyte®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful agents include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), wytensin. (commercially available as Guanabenz acetate®), tenex (commercially available as Guanfacine hydrochloride®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The present invention may include agents useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, and Novolin®); and HPV treatment, such as Human papillomavirus vaccine (commercially available as Gardasil®); immunosuppressants, including cyclosporine (commercially available as Gengraf®, Neoral®, Sandimmune®, and Apo-Cyclosporine®).

Agents useful in the present invention may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), Synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and EstroGel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), and norethindrone acetate (commercially available as Aygestin); and muscle relaxants, including cyclobenzaprine hydrochloride (commercially available as Flexeril®), tizanidine (commercially available as Zanaflex®), and hyoscyamine sulfate (commercially available as Levsin®).

Agents useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CR®), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present invention may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), and paroxtine hydrochloride (available as Paxil®), aripiprazole (commercially aavialbe as Abilify®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SR®, and Wellbutrin XR®), and olanzapine (commercially available as Zyprexa®).

Agents useful herein may also include uric acid reduction treatment, including allopurinol (commercially available as Zyloprim®); seizure medications, including gabapentin (commercially available as Neurontin®), ethotoin (commercially available as Peganone®), and topiramate (commercially available as Topamax®); treatment for shingles, such as zoster vaccine live (commercially available as Zostavax®); skin care medications, including calcipotriene (commercially available as Dovonex®), isotretinoin (commercially available as Accutane®), hydrocortisone/iodoquinol (commercially available as Alcortin ®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solagé®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other agents useful herein may include Sleep disorder medications, including zaleplon (available as Sonata®) and eszopiclone (available as Lunesta®), zolpidem tartrate (commercially available as Ambient, Ambien CR®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Films of the present invention may further include agents useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Wasted constituent in the manufacturing process results in direct loss of profitability and efficiency. As such, it is desirable to limit any waste in the manufacturing process in order to conserve costs and promote efficiency in production. One way to minimize cost is to limit the amount of wasted film composition. Some waste may be from the formation and processing of the film into the final individual-sized delivery modules, while other scrap may be due, for example, to malfunctioning packaging equipment. This may be attributed to wasted film composition in either the mix or batch (liquid) or the final individual film dose product.

The present invention embodies methods of optimizing film production. As used herein, the term "optimizing" refers to processes and methods that minimize waste that may be generated during the formation of the film product (thus, resulting in a higher yield percentage). For example, one may desirably adjust the parameters of manufacturing and production in order to minimize the scrap film, which is one waste product. Through the present invention, production parameters may be adjusted based on various system components, known variables, and devisable factors. Thus, the present invention of optimizing film production may result in various advantages, including a greater efficiency in manufacturing, including less wasted product, and lower cost per individual film strip or sheet dosage. Thus, in focusing on reducing the attributable errors and scrap in the processing and manufacturing steps, a greater number of film strips or film sheets may be produced at the same, or lower total cost in a given process design.

To appreciate the present invention, it is helpful to understand the general characteristics of individual film strip doses, the processing and manufacturing of the film strips, as well as the factors and variables, which may be related to the methods and systems of the present invention. It is known and appreciated that additional characteristics of film strips and methods of making the same are possible and foreseeable in combination with desirable properties and characteristics listed herein, as may be desired. Thus, the present disclosure, by way of example, in no way limits the various embodiments of the present invention.

Each individual film strip dose may be characterized in that it may have a strip weight, a strip width, a strip length, and a strip thickness. These parameters may be varied in order to yield a dosage, which dissolves, for example, quickly, slowly, over a period of predetermined length, and combinations thereof. Further, the size and compositional make-up of the dosage may attribute different levels or amounts of active ingredient(s) or agent(s), which may be delivered to an individual. Thus, various film strip shapes and varying thicknesses are included in the film strip dosages of the present invention. In order to manufacture a film strip which meets the rigors for commercialization and regulatory approval, factors including consistency, quality, and efficacy must be maintained throughout processing and manufacture.

Forming the Film

A film forming matrix, including, for example, a film-forming polymer, polar solvent, any additives, and the active ingredient may be formed in a number of steps. For example, the various components may all be initially added together, or pre-mixes of different materials may separately be prepared. One advantage of a pre-mix is that all ingredients, except for the active, may be combined in advance, with the active added just prior to formation of the film. This is especially important for actives that may degrade with prolonged exposure to water, air or another polar solvent.

Mixing techniques may play a role in manufacturing of a pharmaceutical film that is suitable for commercialization and regulatory approval. For example, if air is trapped in the composition during the mixing process (or later during the film making process), it can leave voids in the film product as the moisture evaporates during the drying stage. This may result in film collapse around the voids, which causes an uneven film surface and ultimately, attributes to a non-uniform final film product, which may have inconsistent properties and component distribution. Uniformity may still be affected even if the voids in the film caused by air bubbles do not collapse. This situation also provides a non-uniform film in that the spaces, which are not uniformly distributed, are occupying area that would otherwise be occupied by the film composition. Once uniformity is compromised, having a consistent dosage of active from one strip to another is much more difficult to achieve.

FIG. 1 shows an apparatus 20 suitable for the preparation of a pre-mix, addition of an active, and the subsequent formation of a film or sheet. The pre-mix or master batch 22, which includes the film-forming polymer, polar solvent, and any other additives except a drug active may be added to the master batch feed tank 24.

Figure 5:
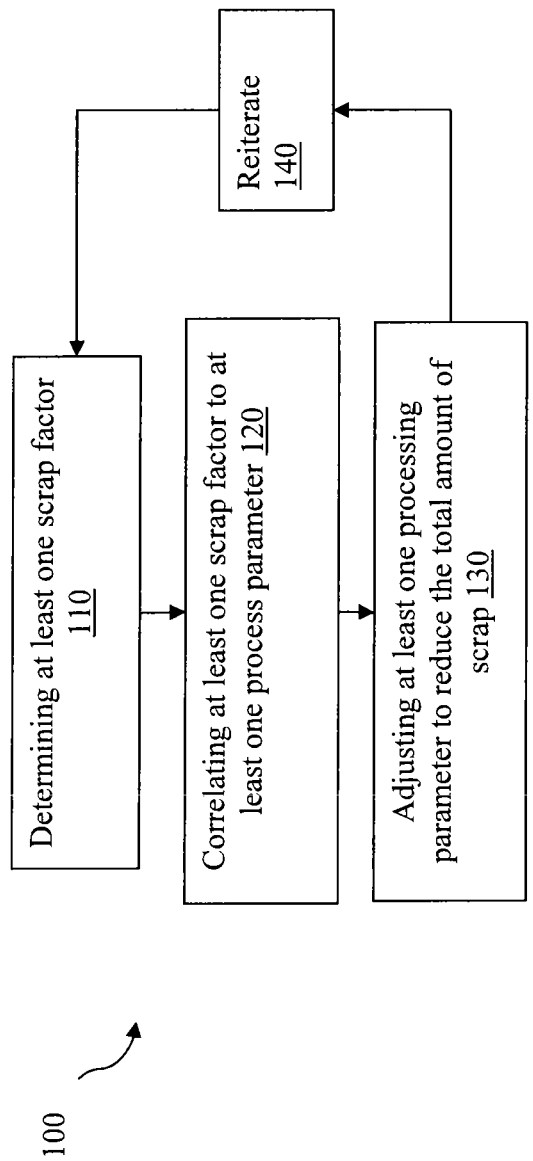
FIG. 5 is a flow chart of a method for determining and reducing the amount of scrap resulting from the processing of ingestible film or sheet products.

The components for pre-mix or master batch 22 are desirably formed in a mixer (not shown) prior to their addition into the master batch feed tank 24. Then a pre-determined amount of the master batch may be controllably fed via a first metering pump 26 and control valve 28 to either or both of the first and second mixers, 30, 30'. The present invention, however, is not limited to the use of two mixers, 30, 30', and any number of mixers may suitably be used. Moreover, the present invention is not limited to any particular sequencing of the mixers 30, 30', such as parallel sequencing as depicted in FIG. 5 (discussed below), and other sequencing or arrangements of mixers, such as series or combination of parallel and series, may suitably be used.

The required amount of the drug or other ingredient, such as a flavor, may be added to the desired mixer through an opening, 32, 32', in each of the mixers, 30, 30'. Desirably, the residence time of the pre-mix or master batch 22 is minimized in the mixers 30, 30'. While complete dispersion of the drug into the pre-mix or master batch 22 is desirable, excessive residence times may result in leaching or dissolving of the drug, especially in the case for a soluble drug. Thus, the mixers 30, 30' are often smaller, with lower residence times required to achieve the desired level of mixing, as compared to the primary mixers (not shown) used in forming the pre-mix or master batch 22.

After the drug has been blended with the master batch pre-mix for a sufficient time to provide a uniform matrix, a specific amount of the uniform matrix may then fed to the pan 36 through second metering pumps, 34, 34'. A metering roller 38 may be used to determine the thickness of the wet film 42 and apply it to the application roller. Thus, the metering roller 38 may be adjusted to form a very thin film, a thick film, or other variations as may be desired. Once the wet film 42 is formed on the substrate 44, the film 42 may be carried away or conveyed onto further processing via the support roller 46.

The combination of the multi-component matrix, which includes the polymer, water, and an active (or other components as desired), may be formed into a sheet or film used other equipment, instruments, or techniques commonly known in the art besides those depicted in FIG. 1.

In addition to the aforementioned film forming method, any method known in the art such as extrusion, coating, spreading, casting, spraying or drawing the multi-component matrix may be used to form the film or sheet. Although a variety of different film-forming techniques may be used, it is desirable to select a method that will provide a self-supporting, flexible film, such as reverse roll coating. The flexibility of the film allows for the sheets of film to be rolled and transported without breaking once they are formed. Film rolls may be stored for a period of time prior to being cut, or may be easily transported across a room or facility. Desirably, the films will also be self-supporting or able to maintain their integrity and structure in the absence of a separate support. Furthermore, the films of the present invention may be selected from materials that are edible, ingestible, biodegradable, biocompatible, and or pharmaceutically acceptable.

Multi-layered films or sheets may be formed by co-extruding more than one combination of components (of the same or different combination), or by a multi-step coating, spreading, casting, drawing, or combinations thereof As another example, a multi-layered film may also be achieved by coating, spreading, or casting a combination onto an already formed film layer.

Coating or casting methods are particularly useful for the purpose of forming the films of the present invention. Specific examples of forming the film may include: (1) reverse roll coating; (2) gravure coating; (3) immersion or dip coating; (4) metering rod or meyer bar coating; (5) slot die or extrusion coating; (6) gap or knife over roll coating; (7) air knife coating; (8) curtain coating; or combinations thereof. Combinations of one or more of the aforementioned may be employed when the formation of a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller may be wiped off by a doctor blade and the coating is then deposited onto the substrate as it passes between the engraved roller and a pressure roller. Offset Gravure is common, where the coating is deposited on an intermediate roller before transfer to the substrate.

In the simple process of immersion or dip coating, the substrate is dipped into a bath of the coating, which is normally of a low viscosity, to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "extrusion" and in this case, the line speed is frequently much faster than the speed of the extrusion. This enables coatings to be considerably thinner than the width of the slot. In addition, slot die coating may be beneficial in that it may reduce or altogether eliminate the requirement for edge trimming from the film. A similar embodiment includes using parallel slots to coat film products in the same coating head. In this embodiment, it is possible to coat with one solution without an active on one side of the coating head until the proper gap setting and oven temperature is reached. At this point, the coating head can be switched to the active side, allowing the active to be coated at the right setting and oven temperature.

The gap or knife over roll process relies on a coating being applied to the substrate, which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

While viscosity, uniformity, stability, and casting are important aspects of the film formation process, the method of removing the moisture from the wet film to create a dried product is also an important factor. That is, a quick, controlled drying process ensures that the uniformity of content of the film is rapidly achieved and will be maintained within the film once the film is dry. In one embodiment, a viscoelastic mass is rapidly formed, which "locks in" the uniformity of content of the film matrix. The viscoelastic mass may then be further dried to fully form the self-supporting film dosage.

Once the film strip is formed, any water or aqueous components of the wet film are desirably removed in order to provide a final product which is in a self-supporting condition, and which may maintain a certain shape or conformation. Further, the active agent may desirably be evenly or uniformly distributed throughout the film strip product. In order to promote an exact dosing of active ingredient or agent in each film strip, it may be desirable to make each film strip substantially uniform in surface and consistency. As such, it may be desirable to control one or more processing parameters in order to ensure that air bubbles, ridges, and or pockets may be eliminated prior to and during the film formation and the drying process (if any) employed therewith.

Processing the Wet Film Product to Remove Excess Moisture

The films of the present invention may contain particles that are sensitive to temperature, such as flavors, which may be volatile, or drugs, which may have a low degradation temperature. In such cases, the drying techniques used to form the film may be varied in order to adequately dry the uniform films of the present invention. Drying the wet film product may be desirable in order to remove excess moisture from the film product.

A modification to the drying step may be to reduce the amount of time that a wet film is potentially exposed to contaminants, and the amount of time from processing to packaging (i.e. a more efficient manufacturing process). Excess water, solvent, or moisture in the film product may contribute to a non-uniform product and/or degradation of active components within the film or sheet. Drying may be through the evaporation of excess water at ambient or other desired temperatures over a length of time. The film may be dried at low or negative pressures (i.e. vacuum dried), or the film may be dried by air blowers, fans, and the like. The drying step may reduce any aggregation or conglomeration of the film components as it is formed into a solid structure. The drying process may further permit exposure of the film to temperatures above that at which the active ingredient typically would degrade without loss of a desired level of activity. Any of these drying methods may be varied as desired.

The wet film may optionally be dried using controlled bottom drying or controlled microwave drying, desirably in the absence of external air currents or heat on the top (exposed) surface of the film 48. Controlled bottom drying or controlled microwave drying advantageously allows for vapor release from the film.

Conventional convection air drying from the top is not preferably employed as it initiates drying at the top uppermost portion of the film, thereby forming a barrier against fluid flow, such as the evaporative vapors, and thermal flow, such as the thermal energy for drying. Such dried upper portions serve as a barrier to further vapor release as the portions beneath are dried, which results in non-uniform films. As previously mentioned, some top air flow can be used to aid the drying of the films of the present invention, but it preferably does not create a condition that would cause particle movement or a rippling effect in the film, both of which would result in non-uniformity. If top air is employed, it is preferably balanced with the bottom air drying to avoid non-uniformity and prevent film lift-up on the carrier belt. A balanced top and bottom air flow may be suitable where the bottom air flow functions as the major source of drying and the top air flow is the minor source of drying. The advantage of some top air flow is to move the exiting vapors away from the film thereby aiding in the overall drying process. The use of any top air flow or top drying, however, is preferably balanced by a number of factors including, but not limited, to rheological properties of the composition and mechanical aspects of the processing. Any top fluid flow, such as air, also preferably does not overcome the inherent viscosity of the film-forming composition. In other words, the top air flow cannot break, distort or otherwise physically disturb the surface of the composition. Moreover, air velocities are desirably below the yield values of the film, i.e., below any force level that can move the liquids in the film-forming compositions. For thin or low viscosity compositions, low air velocity must be used. For thick or high viscosity compositions, higher air velocities may be used. Furthermore, air velocities are desirably low so as to avoid any lifting or other movement of the film formed from the compositions.

In bottom drying, the evaporating vapors more readily carry heat away from the film as compared to top drying which lowers the internal film temperature. Such lower internal film temperatures often result in decreased drug degradation and decreased loss of certain volatiles, such as flavors.

During film preparation, it may be desirable to dry films at high temperatures. High heat drying produces uniform films, and leads to greater efficiencies in film production. Films containing sensitive active components, however, may face degradation problems at high temperatures. Degradation is the "decomposition of a compound . . . exhibiting well-defined intermediate products." The American Heritage Dictionary of the English Language ($4^{th}$ ed. 2000). Degradation of an active component is typically undesirable as it may cause instability, inactivity, and/or decreased potency of the active component. For instance, if the active component is a drug or bioactive material, this may adversely affect the safety or efficacy of the final pharmaceutical product. Additionally, highly volatile materials will tend to be quickly released from this film upon exposure to conventional drying methods.

Degradation of an active component may occur through a variety of processes, such as, hydrolysis, oxidation, and light degradation, depending upon the particular active component. Moreover, temperature has a significant effect on the rate of such reactions. The rate of degradation typically doubles for every 10° C. increase in temperature. Therefore, it is commonly understood that exposing an active component to high temperatures will initiate and/or accelerate undesirable degradation reactions.

During the drying process of the present invention, several factors produce uniformity within the film while maintaining the active component at a safe temperature, i.e., below its degradation temperature. First, the films of the present invention have an extremely short heat history, usually only about minutes, so that total temperature exposure is minimized to the extent possible. Second, the films are controllably dried to prevent aggregation and migration of components, as well as preventing heat build up within. Third, the films are desirably dried from the bottom, as controlled bottom drying, as described herein, prevents the formation of a polymer film, or skin, on the top surface of the film. As heat is conducted from the film bottom upward, liquid carrier, e.g., water, rises to the film surface. The absence of a surface skin permits rapid evaporation of the liquid carrier as the temperature increases, and thus, concurrent evaporative cooling of the film. Due to the short heat exposure and evaporative cooling, the film components such as drugs or volatile actives remain unaffected by high temperatures. In contrast, skinning on the top surface traps liquid carrier molecules of increased energy within the film, thereby causing the temperature within the film to rise and exposing active components to high, potentially deleterious temperatures.

Figure 2:
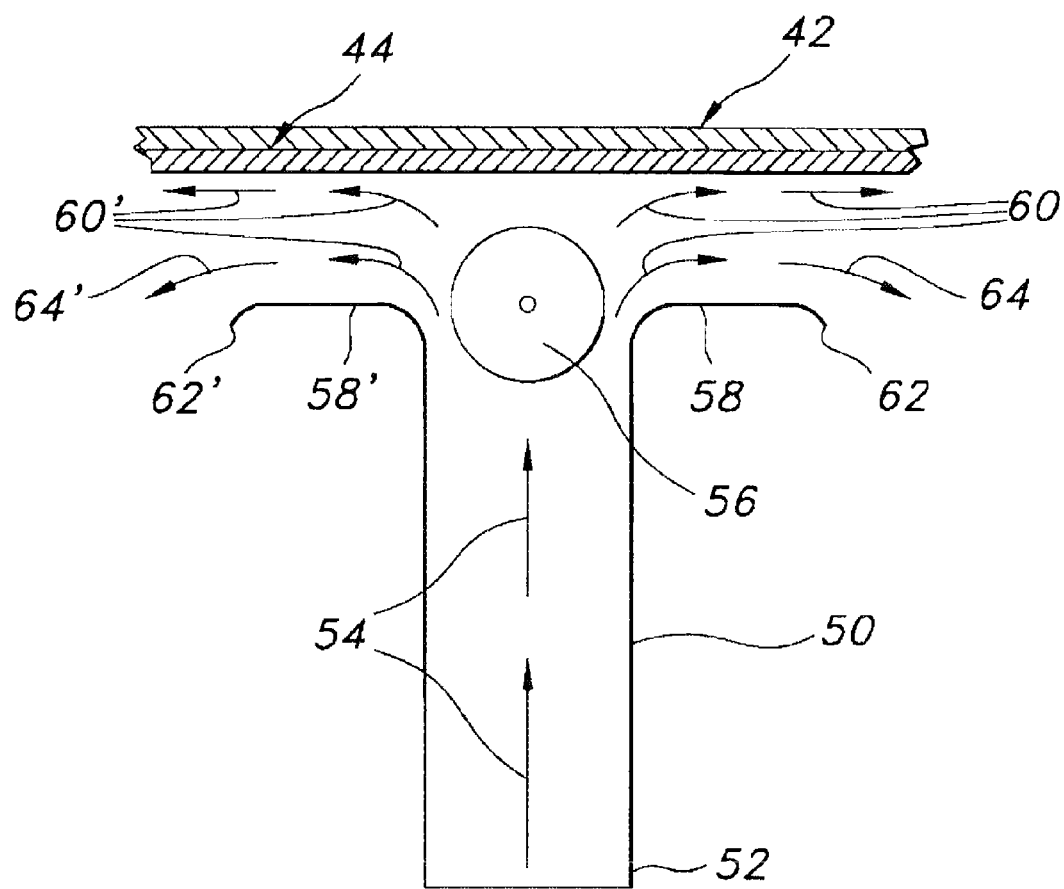
FIG. 2 is a schematic view of an exemplary drying step for the film sheet of the present invention.

Although the inventive process is not limited to any particular apparatus for the above-described desirable drying, one particular useful drying apparatus 50 is depicted in FIG. 2. Drying apparatus 50 is a nozzle arrangement for directing hot fluid, such as but not limited to hot air, towards the bottom of the film 42, which is disposed on a substrate 44. The substrate 44 may include any material on which the film 42 can be coated. Two preferred substrates include Mylar and silicone coated paper, however other substrates may be used if desired. For example, the substrate may include a metal belt, any number of polymer materials, other films, and the like. In one embodiment, the substrate may include a packaging foil, which may allow the film to be applied to the substrate and packaged immediately after drying, without the need to separately form and package the film 42.

In one embodiment, depicted in FIG. 2, hot air is allowed to enter the entrance end 52 of the drying apparatus and travel vertically upward, as depicted by vectors 54, towards an air deflector 56. The use of an air deflector 56 is optional, but may be desired, as it is capable of redirecting the air movement to minimize upward force on the film 42. Thus, the air is tangentially directed, as indicated by vectors 60 and 60' as the air passes by air deflector 56 and travels through chamber portions 58 and 58' of the drying apparatus 50. With the hot air flow being substantially tangential to the film 42, lifting of the film as it is being dried is thereby minimized.

While the air deflector 56 is depicted as a roller type of device, other devices and geometries for deflecting air or hot fluid may suitable be used, including, for example, cylindrical, triangular, and other type of geometries for deflecting fluid. The exit ends 62 and 62' of the drying apparatus 50 are desirably flared downwardly. Downward flaring provides a downward force or downward velocity vector, as indicated by vectors 64 and 64', which tend to provide a pulling or drag effect of the film 42 to prevent undesirable lifting of the film 42. Lifting of the film 42 may not only result in non-uniformity in the film or otherwise, but may also result in non-controlled processing of the film 42 as the film 42 and/or substrate 44 lift away from the processing equipment.

Figure 3:
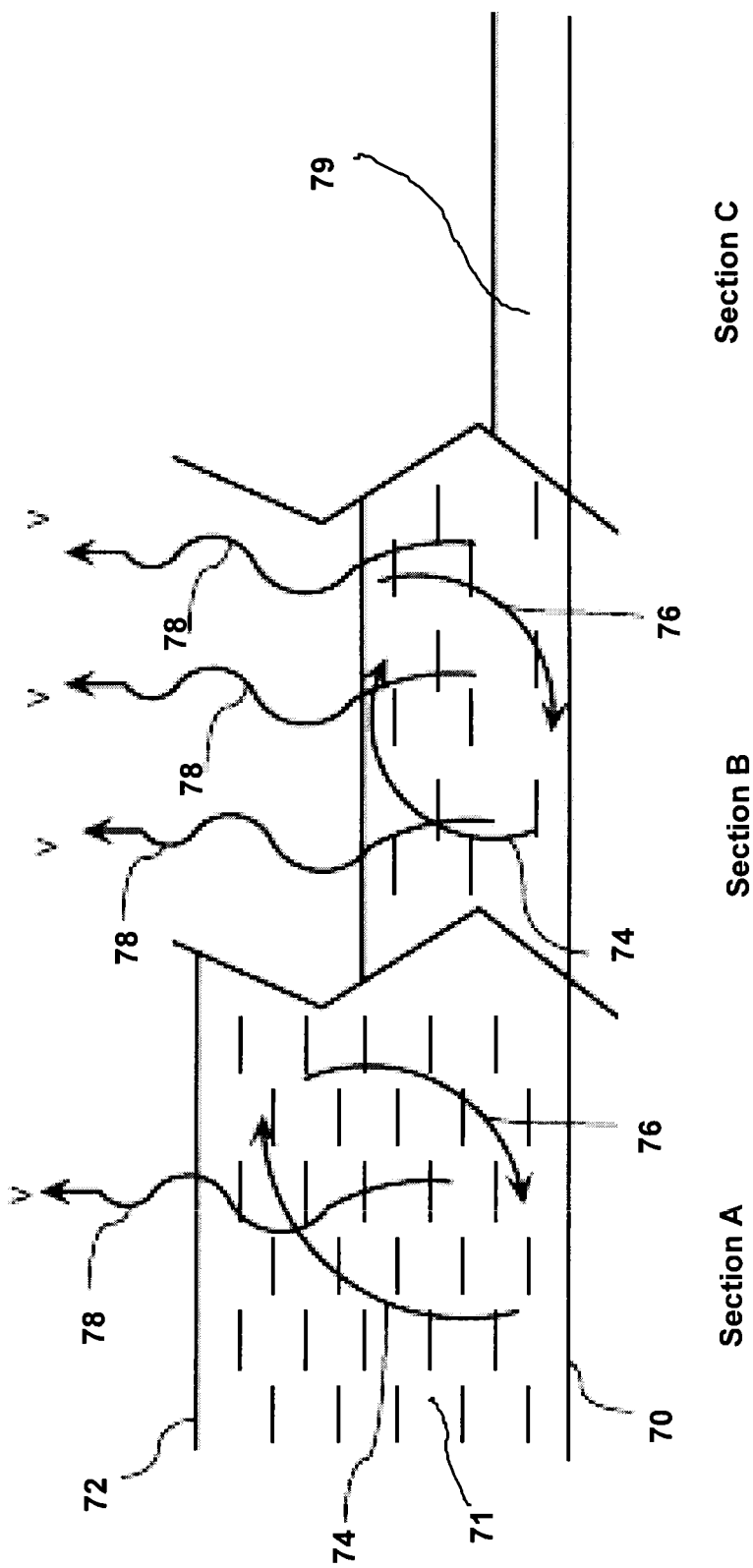
FIG. 3 is a representation of a drying process of the present invention.

FIG. 3 is a sequential representation of a drying process useful in the present invention. After mechanical mixing, the film may be placed on a conveyor for continued thermal mixing during the drying process. At the outset of the drying process, depicted in Section A, the wet film forming matrix 71 is heated, optionally from the bottom 70, as it is travels via conveyor (not shown). Heat may be supplied to the film by a heating mechanism, such as, but not limited to, the dryer depicted in FIG. 2.

As the film is heated, any liquid carriers, or volatiles ("V") present in the wet film, begin to evaporate, as shown by upward arrow 78. Thermal mixing also initiates as hotter liquid, depicted by arrow 74, rises and cooler liquid, depicted by arrow 76, takes its place. Because there is no skin formation on the top surface 72 of the film 1, (as shown in Section B), the volatile liquid continues to evaporate 78 and thermal mixing 74/76 continues to distribute thermal energy throughout the film. Once a sufficient amount of the volatile liquid has evaporated, thermal mixing has produced uniform heat diffusion throughout the wet film forming matrix 71. The resulting dried film 79 is a visco-elastic solid, as depicted in Section C. Desirably, the components are locked into a uniform distribution throughout the film. Minor amounts of liquid carrier, i.e., water or solvent, may remain subsequent to formation of the visco-elastic solid 79. If desired, the visco-elastic solid 79 may be dried further without resulting in movement of the particles. As can be seen, during the drying process (i.e., from Section A to Section C), the thickness of the matrix is reduced, due to evaporation of the volatiles present in the matrix 71.

The drying step(s) remove the liquid carriers from the film in a manner such that the uniformity, or more specifically, the non-self-aggregating uniform heterogeneity, that is obtained in the wet film is maintained. The temperature of the oven, the length of drying time and the amount of humidity in the ambient air may be controllable factors in the drying process. The amount of energy, temperature and length and speed of the conveyor can be balanced to accommodate such actives and to minimize loss, degradation or ineffectiveness in the final film. Desirably, the drying oven (or ovens) is first turned on and is allowed to run until the temperature within the oven has stabilized at the set point before coating is started. The length of the drying oven may be altered as necessary to achieve the drying desired. For example, when a smaller batch size is used, or when the coating is narrow, the length of the drying time may be reduced. The drying time may be changed via the speed at which the film travels, or the number of ovens through which the film travels. For example, in one embodiment, the drying process includes passing the film through at least two ovens, or at least five ovens. Any number of ovens may be used in the drying process to achieve the desired film.

Monitoring and control of the thickness of the film also contributes to the production of a uniform film by providing a film of uniform thickness. The thickness of the film may be monitored with gauges, such as Beta or Gamma Gauges. A gauge may be coupled to another gauge at the end of the drying apparatus, i.e. drying oven or tunnel, to communicate through feedback loops to control and adjust the opening in the coating apparatus, resulting in control of uniform film thickness. Desirably, the film is formulated so that the dimensional changes incurred during drying are to the film's thickness and not its width. As such, monitoring of the film's thickness may be helpful in maintaining a suitable product.

Cutting and Packaging the Sheet or Film Product

Once the film or sheet is mixed, formed, and dried into a thin film or sheet product, the film or sheet may be cut into certain shapes, dimensions, and the like, and packaged in a desirable contaminant-preventing and shelf-life promoting packaging material. In preferred embodiments, the film is maintained in a package that is suitable for protecting products including active components, and most desirably is approved by any regulatory agency that may be applicable.

In the cutting process, the equipment may generally include a slitter and a package machine. The slitter cuts or trims the edges of the film product as desired, necessarily resulting in some degree of scrap. The film may be shaped and sized into a continuous roll of film, or it may be cut into individual pieces of film product. Once the film product is cut, the cut film product may be delivered directly to the customer.

In some embodiments, after the film is cut, the cut film may be provided to an outside packager, where the material may be finally cut to its desired length (i.e., film strips) and may be placed into an individual package, such as a cassette or other protective packaging. Still other cut products may be provided to contract packagers who may then cut the film product to the desired length, and then package the cut film products in foil pouches with custom built pouching machine. In a preferred embodiment, after cutting the sheet of film into individual film products, the film products are packaged in individual foil pouches via a pouching machine. These individually packaged products may then be distributed to customers or distributors for use. Any combination of a coating apparatus, slitter and pouching machine may be used as desired, and in a preferred embodiment, the coating apparatus, slitter and pouching machine are used in combination with each other.

Figure 4:
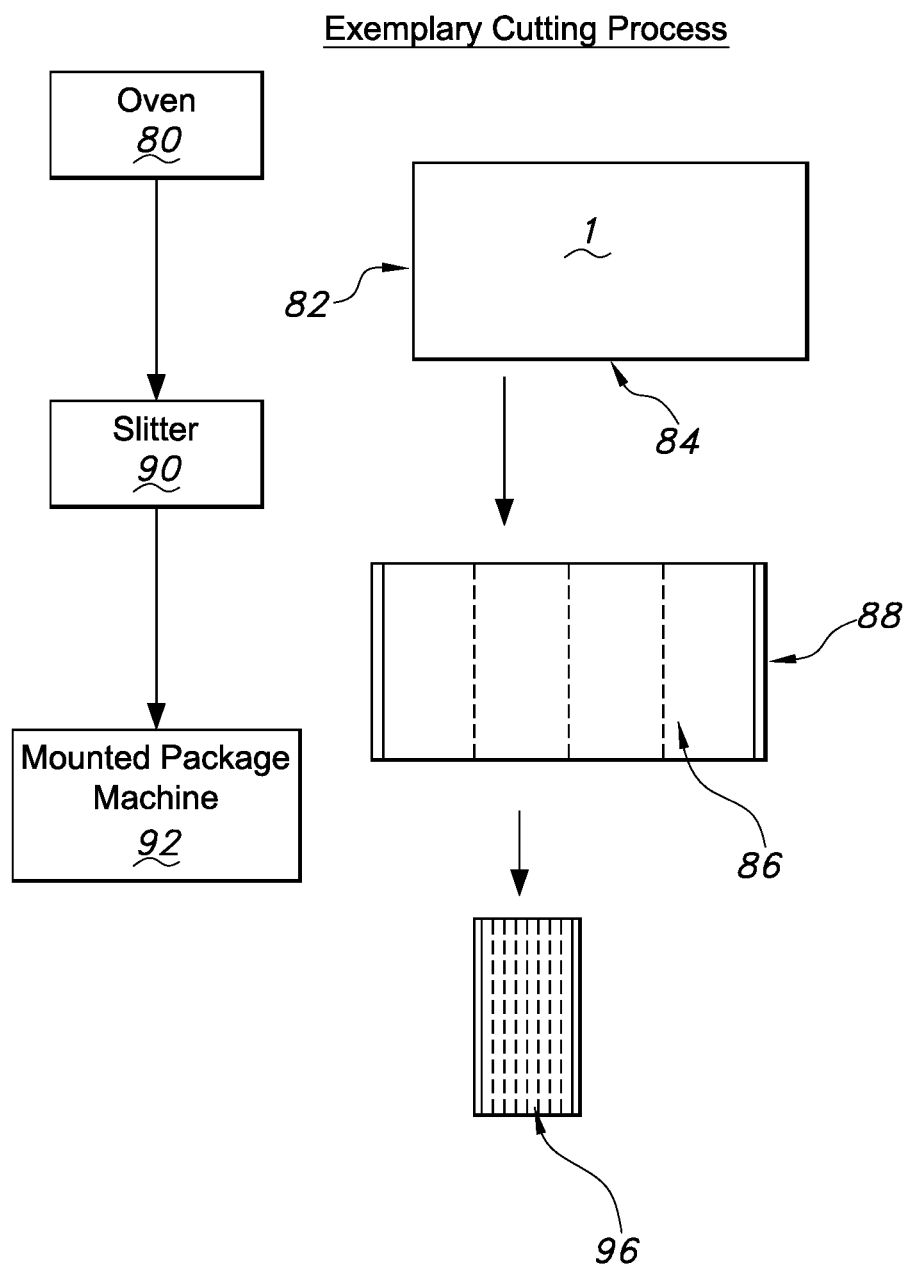
FIG. 4 is a schematic view of the cutting process that may be employed when the film sheet is reduced to individual doses for packaging. An exemplary film sheet of film is shown as it goes through the cutting steps.

FIG. 4 generally depicts a schematic for cutting or trimming a film product down into individual film strips or sheets. In FIG. 4, the drying apparatus 50 (referred to in FIG. 2) is depicted as an oven 80. Generally, once the film 1 is mixed and reverse roll coated into the film sheet, the film sheet 1 is dried. Here, the sheet is oven-dried by oven 80.

The exemplary film sheet 1 depicted in FIG. 4 has a coated width of about 31" wide (where 1 inch =2.54 cm). Though the sheet 1 is shown as a rectangle, discontinuous regions along the length 82 of the film 1 denote that the film 1 may be of any length, generally dependent upon the batch size, thickness of the film, and coating width 84 of the film 1. Once the sheet 1 leaves the oven 80, the sheet 1 is fed onto the slitter 90. On the slitter 90, an outer edge 88 measuring about ½" is trimmed from each side of the sheet 1 in order to remove any inconsistencies along the outer-most edge 88 of the film 1. Then, the slitter 90 also cuts the sheet 1 down into individual rolls 86, or "daughter" rolls, as the rolls stem from the same mother sheet. The daughter rolls are labeled 86. Thus, once the outer-edge trim 88 (measuring about ½") is removed from each edge, the film sheet 1 is a total of 30" wide, while each daughter roll 86 is roughly ¼ of the total width, or, in one embodiment, about 7.5" wide, per roll. The cuts on the sheet which yield the daughter rolls 86 are depicted as dashed lines on FIG. 4, as the daughter rolls 86 are further processed. The outer-edge trims 88, however, are removed from the sheet and discarded as scrap. It should be noted that the rolls of film 86 formed from the sheet of film are generally self-supporting and flexible in nature, such that the films may be rolled over and onto itself to form a daughter roll. These rolls may be stored; however, ultimately, these rolls are preferably processed by feeding the rolls onto the package machine 92.

As the roll 86 is fed onto the package machine 92, the package machine 92 may also perform a cutting function. The package machine 92 may trim another section (approximately ¼") off each side, to yield another about ½" of scrap. Thus, after this cutting, the roll is trimmed down to about 7" width. The package machine also cuts each daughter roll down into individual lanes 96. As depicted in FIG. 4, the daughter roll 86 may be cut into a plurality of individual lanes. In one embodiment, the daughter roll 86 may be cut into about 8 lines, such that each lane has a total with of ⅞". Thus, in this embodiment, each individual film strip or sheet dosage may have a total width of ⅞". Other sizes may be used if desired, for example, the daughter roll may be cut into from about 2 to about 10 lanes, if desired. Each lane 96 may then be cut along a predetermined length in order to yield the finished film strip product. Typically, the film strip is immediately packaged once the final cut is made from the individual lane, although the cut film strip may be stored until packaged.

Optimization of Film or Sheet Production Method(s)

While various processing parameters have been discussed in the aforementioned paragraphs, the present inventors have determined a set of common denominators or variables in processing techniques that may be controlled in order to optimize the manufacturing and processing of film or sheet dosage production while minimizing the scrap (or waste) that is produced. These variables are defined in the following Table 1, which sets forth the variable abbreviation, a description of the variable, the source of the variable, and the units in which the variable is expressed:

TABLE I

List of Variables

| Variable | Description | Source | Units |
|---|---|---|---|
| $L_O$ | Oven Length | Equipment Train | Meters |
| $V_M$ | Mixer Volume | Equipment Train | Liters |
| $W_P$ | Packaging Roll Width | Equipment Train | Meters |
| $N_S$ | Number of slit rolls/master roll | Independent Variable | No Units |
| $W_C$ | Coating Width | Independent Variable | Meters |
| $W_{PT}$ | Packaging Trim Width | Independent Variable | Meters |
| $W_{ST}$ | Slitting Trim Width | Independent Variable | Meters |
| $\% S_F$ | Formula % Solids | Formulation | % |
| $C_{Si}$ | Coating Solution (Batch Size) | Formulation | Kg |
| $C_T$ | Total Coated Film Area | Formulation | Square Meters |
| $C_W$ | Coating Weight | Formulation | Kg/Square Meter |
| $\% S_M$ | Measured % Solids | Empirical Data | % |
| K | Coating Loss Parameter | Empirical Data | No Units |
| $P_{SS}$ | Packaging Start/Stop Loss | Empirical Data | Meters |
| $S_{SS}$ | Slitting Start/Stop Loss | Empirical Data | Meters |
| $\% W_{PT}$ | % Packaging Trim Width | Calculated | Meters |
| $\% M_{LM}$ | % Mixing Losses Mass | Calculated | Kg |
| $\% P_{SS}$ | % Packaging Start/Stop Loss | Calculated | Meters |
| $\% S_{SS}$ | % Coating Start/Stop Losses | Calculated | Meters |
| $\% W_{ST}$ | % Edge Trim | Calculated | % |
| $C_{Sf}$ | Coated Solution | Calculated | Kg |
| $C_{SS}$ | Coating Start/Stop Losses | Calculated | Meters |
| $L_T$ | Total length of film | Calculated | Meters |
| $M_{LA}$ | Mixing Losses Area | Calculated | Square Meters |
| $M_{LM}$ | Mixing Losses Mass | Calculated | Kg |
| $S_F$ | Solids in Formulation | Calculated | Kg |

TABLE I-continued

List of Variables

| Variable | Description | Source | Units |
|---|---|---|---|
| $S_L$ | Slitting Loss | Calculated | Square Meters |
| $T_S$ | Total Scrap | Calculated | Square Meters |

During production and manufacturing of the film, the various components are mixed in one or more mixers, as previously discussed. The mixer size may be defined by its working volume ($V_M$) in liters. The contents of the mixer may be referred to as the "batch size" or the coating solution volume ($C_{Si}$). The mixer size may be larger than the batch size, as desired. For example, the batch size may be less than the mixer size by including proper agitation in the mixer. Further, the present invention may be employed with various batch sizes, including bench top, pilot plant size, and commercial size applications, with particular reference to batch applications. Each batch includes a percentage of the total weight in solids (percent solids), which may include powders (such as polymers and actives) and non-aqueous liquids (such as ethanol and flavors). Of the total solids, the portion of the liquids which can evaporate in the drying oven is defined as the percentage of volatile liquids (% volatile components). Batch size, as used herein, is an independent variable, which may be used in the inventive formulation to calculate the amount of each component that is needed for a suitable batch. Once the desired batch size is specified, the required total solids ($S_F$) may be calculated by the product of the batch size ($C_{Si}$) and the percentage of solids (% $S_F$) in the below equation (Eq. 1):

$$S_F (kg) = C_{Si} (kg) \times \% S_F \qquad (eq.1)$$

The term "total solids" generally refers to the total weight of solids (including non-aqueous liquids such as flavors) in the pre-mix batch. The total solids is intended to be measured in kg, but other measurements may be used if desired.

The term "formula percent (%) solids" (% $S_F$) generally refers to the fractional ratio, or percentage of solids out of the total amount of the pre-mix batch, measured in a fractional percent. Formula percent solids is the fraction of total solids (kg), including both dry solids and non-aqueous ingredients such as flavors, out of the total coating solution (kg) in the mixer (which is then multiplied by 100 to give a percentage).

The term "measured % solids" (% $S_M$) refers to the measurement of percentage of solids in the coating solution, which may be measured by a suitable loss-in-weight instrument. The measured percentage of solids is intended to not include all of the volatile components of the formula, such as flavors, but only those solids that are not driven off by the measurement.

Mixing Losses

As used herein, the term "mixing scrap" generally refers to the scrap material that may be attributed to the mixing process. This term includes, for example, material that is lost and not recoverable because it coats the tank and/or the hoses, and ultimately is not transferred to the film. Scrap for mixing is measured in kg of solution, which is a function of the surface area of the mixer and/or hoses, which is correlated to the size of the mixer. The loss is generally a function of the mixer design, size and plumbing used to connect the equipment to the coater. In order to apply this optimization to a given coating line, the mixer(s) used in the process should be evaluated, and the amount of solution lost correlated to the mixer size.

Once the amount of lost solution (mixing scrap) ($M_{LM}$) is identified, one can then calculate the % lost solution (% $M_{LM}$) by the following equation (Eq. 2):

$$\% M_{LM} = M_{LM} (kg) / C_{Si} (kg) * 100 \qquad (eq. 2)$$

In order to convert Scrap for mixing into a comparable number (with the other scrap factors, including Coating and Slitting) it may be useful to convert Scrap for Mixing in kg into an area, (or $m^2$). Therefore, assuming that the total mass of lost solution is converted into a coating, one could simply multiply the percentage of mixing loss and the total area of film produced ($C_T$) to get the area loss ($M_{LA}$) in square meters (Eq. 3):

$$M_{LA} = \% M_{LM} * C_T (m^2) \qquad (eq. 3)$$

Coating Losses

Once the film-forming composition is completely processed, it may then be coated or otherwise laid out into a desired film width, and then dried to form the final film. As explained above, the film may be coated, rolled, extruded, sprayed, or any other desired means of laying out the composition into a film form. Further to the present invention, if desired, the actives, polymers, and other film-forming matrix components may be formed into a large sheet of material prior to processing for packaging. The sheet may be coated, rolled, extruded, spread, or otherwise dispersed onto a generally flat area for drying prior to further processing and packaging.

The "coated Solution" ($C_s$, measured in kg) is the amount of solution that becomes part of the final dosage form, and may be defined by the following formula (Eq. 4):

$$C_{Sf} (kg) = C_{Si} (kg) - M_{LM} (kg) \qquad (eq. 4)$$

The term "coating solution" generally refers to the completed mixture of all film-forming components, which are mixed and ready to be coated, cast, extruded, rolled, or otherwise spread in order to form a wet film or sheet. The term "coated solution" generally refers to the wet film product that has been formed, but has not yet completed drying. The coated solution may be any size and thickness desired to achieve the intended final product size.

The "Scrap for Coating" is generally a function of the coating width of the film sheet, i.e. the film sheet formation by dispensing the liquid matrix into a wet sheet (pre-drying). The term "scrap for coating" as used herein generally refers to the scrap that is attributable to forming the film, including the drying step. An example of scrap for coating may generally include the stop scrap and/or the start-up scrap, and the scrap which results from film product which is not completely set or which does not fully dry (for example, if the oven is not optimized prior to the drying process beginning) Start-up scrap may include the very beginning length of the wet sheet, which may not fully dry into a formable film. Start-up scrap may be typically 80-100 m in length, regardless of the width of the material employed. In part, this is because the oven should first come to a steady state to impart drying through a phase shift to the wet film. Thus, the thickness of the film or sheet, as well as the moisture content, should desirably be consistent over a given length of film. This consistency helps promote a uniform product having the desired level of dispersed active throughout the film, i.e., a film that has uniformity of content. Scrap for Coating is measured as surface area ($m^2$).

The start/stop scrap ($C_{ss}$) for coating may be defined by the following formula (Eq. 5)

$$C_{SS}(m^2)=K*L_O(m)*W_C(m) \tag{Eq. 5}$$

where K is an empirical constant developed by evaluating historical data for a specific coating system and $L_o$ is the length of the drying oven. The constant K is the number of oven passes required to reach steady state at the required in-process conditions in drying the film.

The term "coating width" ($W_C$) generally refers to the width of a sheet of film before it is dried (i.e., after it is cast or rolled), where the width is measured from side to side of the cast film as it exits the rollers on the substrate. Coating width and coating length may be variable parameters that may be adjusted to optimize yield (or to minimize waste). For example, the coating width may generally be constant for a given manufacturing apparatus, while the coating length may be variable. Alternatively, the coating width may be variable and the coating length generally constant. In other embodiments, both the coating width and coating length may be variable, or both may be constant.

As the batch size increases, the fixed scrap generally stays the same and the variable scrap generally increases. As the coating width is increased, the coating scrap increases but the trim scrap decreases.

The term "Coating Weight" ($C_W$) generally refers to the weight per unit area of the film and is generally proportional to the thickness of the coating, which may be varied based on the coating method and equipment employed.

The term "total length of coated film" generally refers to the total length of the final film product, measured as it is collected on master rolls at the end of the coating equipment. The total length of coated film may be a function of the batch size, thickness of the coating, and width of the coating. Thus, after the film is formed, the film may be cut to yield an identical dosage size and a uniform product surface, in predetermined shapes and dimensions, in order to be fitted into the desired dosage and/or packaging.

The Total Length of Coated Film ($L_T$) may be defined by the following equation (eq. 6):

$$L_T(m)=C_{Si}(kg)*\%S_M/(C_W(kg/m^2)*W_C(m)) \tag{eq. 6}$$

For formulations where there are many volatile components in the coating solution, the percent of solids measurement may not be indicative of the actual percent of solids that exits the oven in the form of film. In such an instance, the specific formulations must be evaluated to determine the actual square meters of film each formulation will produce.

Slitting Losses

The term "slitting losses" as used herein generally refers in part to the scrap that is a result of cutting a formed and dried film sheet into smaller rolls from which the individual doses are to be packaged. The term "edge trim" as used herein generally refers to the outermost edge of the "coating width" of the coated film, which is trimmed off.

Trimming the edges of the coating width (i.e., the "edge trim") reduces or altogether eliminates inconsistencies along the outermost edges of the film due to the coating/casting/rolling process. Such inconsistencies are removed in order to provide a uniform and consistent product. Slitting edge trim is measured as the outside cut from the edge of the film sheet as it goes through the slitter. The width of this cut is an independent variable ($W_{ST}$). The percentage of edge trim scrap is then defined as the width of the edge trim divided by the starting width of the film. As the width of the edge trim is independent of the total film width, the percentage of edge trim scrap is inversely proportional to the coating width, as demonstrated in the below equation (eq. 7):

$$\%W_{ST}=W_{ST}(m)/W_C(m)*100 \tag{eq. 7}$$

Notably, additional scrap ($S_{SS}$) may be produced at the slitter at the startup and shut down of the batch. The length of this scrap is normally constant and independent of film width. The percentage of start/stop scrap (% $S_{SS}$) is therefore inversely proportional to the total length of film (batch size), and is proportional to the width of the film, as set forth in the below equation (eq. 8):

$$\%S_{SS}=S_{SS}(m)/L_T(m)*100 \tag{eq. 8}$$

It will be understood, of course, that there can be other scrap associated with slitting, i.e. web breaks, equipment failures and other processing issues. This other scrap is referred to herein as scrap due to error. Scrap due to error is not a function of batch size or coating width, but tends to be generally random and is therefore not considered in this optimization method. Desirably, there is no scrap due to error, and thus the final product is optimized.

Scrap for slitting ($S_L$) or slitting losses may be defined by the formula (eq. 9):

$$S_L(m^2)=W_{ST}(m)*L_T(m)+S_{SS} \tag{eq. 9}$$

As the edge trim is removed from the sheet, the sheet may also be slit into individual rolls for ease of packaging.

Packaging Losses

In some embodiments, the slit rolls may be fed into a packaging machine for final packaging. In such embodiments, as the slit rolls are fed onto the package machine, each roll may be subjected to another edge trim to remove any final inconsistencies which may have resulted in the transport and or storage of the film. Desirably, such edge trim will be nominal, since the roll has already been trimmed to its desired size. In addition, the package machine may also cut each roll into an individual dosage width. Lengths may be cut as the individual lanes enter the packaging. In general, there are 3 main types of scrap associated with a standard packaging machine. The first type of scrap is packaging edge trim, which is a constant percentage, independent of batch size or coating width. The percentage of packaging edge trim is defined as the width of the packaging edge trim ($W_{PT}$) divided by the width of the slit roll being packaged (eq. 10):

$$\%W_{PT}=W_{PT}(m)/W_P(m)\times100 \tag{eq. 10}$$

The second scrap includes the length of film that is wasted during the start up of the packaging machine. The film used up at the start up of the packaging machine includes film that may be wasted for various alignment and consistency reasons, such as for the alignment of the packaging material, adjustment of printers, adjusting static charges, and other processing parameters. For a given batch, the packaging start up scrap ($P_{SS}$) is desirably a reasonably constant number and independent of batch size or coating width. Therefore the percentage of packaging start up scrap (% $P_{SS}$) is inversely proportional to the batch size (eq. 11), where $N_S$ is the number of slit rolls per master roll:

$$\%P_{SS}=P_{SS}(m)/(L_T(m)*N_S)*100 \tag{eq. 11}$$

The third typical scrap associated with packaging is a result of malfunctions in the process, such as web breaks, printers drifting out of alignment, registration drift of the packaging material and other processing issues. As with the other scrap due to error, this scrap is desirably limited to the least amount possible, and is not a function of the batch size and coating width. Since this error scrap is not a function of the batch size and coating width, it is therefore not pertinent to the optimized yield analysis of the present invention.

Analysis of Data

The term "total scrap" ($T_s$) as used herein generally refers to the total scrap of the film or sheet due to manufacturing, which includes any or all of the scrap lost to mixing, the scrap lost to coating, the scrap lost to slitting and the scrap due to packaging. Total scrap is the total scrap from the processing and trimming of the film dosage products. Total Scrap may be defined by the following formula (eq. 12):

$$T_S (m^2) = M_{LA} (m^2) + ([C_{SS} + S_{SS} + P_{SS}] * W_C) (m^2) \quad (eq.\ 12)$$

By utilizing the various relationships of manufacturing steps as set forth herein, it is possible to optimize the coating width in order to minimize the scrap produced in the manufacturing of film products. Therefore, the basis of the invention is to pick the ideal width to coat at which minimizes the scrap. Through use of the inventive method for optimizing film production, it is possible to optimize the process of film production in order to minimize the scrap byproduct for any sheet or slab of film dosage produced.

Optimization of Scrap

There are four types of scrap attributed to the present method of film production, including: (1) scrap for mixing; (2) scrap for coating; (3) scrap for slitting (or cutting) and (4) scrap for packaging. Of the four types of scrap, scrap for mixing, coating, slitting and packaging, two of the scrap factors are directly tied to the width of the coating. Specifically, the scrap for coating is a function of coating width, which is attributed to the start up and shut down losses associated with the present operating system.

The present method of film production is batch oriented with an oven-based drying step. Achieving the proper consistency through drying is important in the present invention. If the film is not dried to the right consistency, the film may be considered waste, and thus will not be packaged for selling/distribution.

Further, it is noted that changes to the operating parameters may result in a new set of scrap. This is because, after a change to any of the operating parameters is made, the film at the new conditions must first go through the coater (1 coater length), and then the resulting film may be tested for coat weight and moisture, among other final properties. Based on these test results, one can make an adjustment and run another test batch to arrive at the proper final film. This repeated testing obviously results in scrap generated. It is understood by those of ordinary skill that longer ovens have the possibility to generate more scrap through such testing. The processing parameters set forth herein are optimized for specified coat weight and moisture, not for scrap.

While the scrap for mixing is not directly related to the coating width, it should be noted that batch or tank size is often selected based on pre-existing roller/coating equipment, ovens, and packaging equipment, etc. Thus, the coating width may be idealized along with an increased batch size in order to efficiently produce an increased number of film strips while reducing the total scrap (including scrap due to mixing, coating, slitting and packaging).

A method of optimizing self-supporting film production is shown, for example, in FIG. 5. The method of optimizing a self-supporting film dosage 100 includes the steps of: determining 110 at least one scrap factor, correlating 120 at least one scrap factor to at least one processing parameter, and adjusting 130 the processing parameter. Once the processing parameter is adjusted, the method is used to lower or reduce at least one scrap factor. As at least one scrap factor is reduced, there is an additive effect, which desirably results in an overall reduction in the total scrap produced in making a film or sheet product. An adjustment in certain processing parameters, for example, is intended to reduce more than one scrap factor, thus having an additive effect on the reduction of total scrap. This is the case when adjusting one processing parameter affects more than one scrap factor.

The at least one scrap factor may generally refer to one or more of the classes of scrap discussed supra, including, scrap for mixing, scrap for coating, scrap for cutting (slitting) and scrap for packaging. Similarly, within these classes of scrap are subclasses of scrap. For example, the scrap for mixing may generally include the subclasses of the scrap lost to hoses and the scrap lost to coating the mixer. The scrap for coating may generally include the scrap subclasses of the scrap for start-up and shut-down of the film forming process, and scrap for the drying step(s), including oven length and various coefficients related to drying. The scrap for cutting may include the scrap subclasses of the scrap for slitting and the scrap for a packing machine, if used. Other sources of scrap due to error may exist, which are not currently scrap factors in the total scrap formula of eq. 12. Although these error factors are not taken into account in the present invention, these scrap factors may additionally be deemed a scrap factor for purposes of the present invention and incorporated into the consideration of the total scrap for manufacturing self-supporting film products. Some of these error-based scrap factors may also include, for example, scrap lost to volatiles, scrap due to the degradation of the components, and scrap due to packaging loses, and scrap due to non-calibrated equipment and instruments. If desired, these other scrap factors may be included in the optimization method 100 described herein.

The determining step 110 may further include determining a scrap due to mixing factor; determining a scrap due to coating factor; determining a scrap due to slitting (or cutting) factor, determining a scrap due to packaging factor, determining one of the subcategories of scrap factors, and combinations thereof. Scrap factors may be determined by reviewing the losses in the manufacturing process, analyzing the processing parameters for losses in yield, or in comparing the theoretical number of strips to the actual number of strips produced.

The correlating step 120 may be achieved by attributing the at least one scrap factor to one or more processing parameters. The processing parameters generally include the manufacturing specifications for a run. Example processing parameters may include the components used in the batch (solids, liquids, actives, etc.), tank size, length of hoses, film formation equipment, film thickness, film uniformity, film dryness, drying parameters (including equipment, temperature, duration), coating width, coating length, size of the final film product, and combinations thereof, as may be desired. These scrap factor(s) may be correlated to process parameters by incorporating the process parameters into the equations (eq. 1 through 12) previously provided, or alternatively, by identifying the relationship between the scrap factor(s) and the processing parameter(s). The equations may be manipulated in order to define how much scrap is attributed to various process parameters, or alternatively, how process parameters may be modified in order to reduce the amount of scrap associated with one or more process parameters. The equations set forth previously (eq. 1 through 12) may aid in defining the relationship between the processing parameters and the various scrap factors, and in the step 120 of correlating at least one scrap factor to at least one processing parameter in accordance with the method 100.

The adjusting step 130 of the present method may include adjusting at least one processing parameter in order to reduce or lower at least one scrap factor of the manufacturing process. Thus, the adjusting step 130 may include, for example, modifying, eliminating, increasing, or decreasing the characteristics of one or more process parameters in order to put the scrap factor under a desired target or within a desired range.

In one particular example, the coating width of the film sheet may be increased or decreased. Varying the coating width of the film sheet may be performed so as to reduce the amount of edge trim needed to reduce the non-uniform edges from the film sheet 1. Varying the coating width may also reduce the amount of edge trim needed from each slit roll 86 in order to ensure that the end individual lanes are the desired width, for example to fit into the packaging machine properly and into the packaging materials/pouches (see, e.g. FIG. 4). Similarly, the coating width and thickness may be adjusted in order to make a more desirable product or manufacturing process.

As still another example, the adjusting step 130 may further include the step of minimizing a hose length from a tank or mixer, thus holding a control volume of mixed film material to be coated. This minimization of hose length may ultimately reduce the standard amount of material that is lost to the hoses as a result of coating.

As yet another example, the adjusting step 130 may further include increasing a drying temperature, a drying duration, or an oven length in order to promote a desired level of drying in the final film product. The adjusting step 130 seeks to modify one or more processing parameters so as to provide a desirable end product (i.e., one that is uniform and fully dried), while reducing the waste material generated by the process. In some instances, the drying parameters (i.e., temperature, length, duration, etc.) may be increased. In other instances, such parameters may be shortened.

The examples of adjusting provided herein are intended to be non-limiting in nature, and are presented for illustrative purposes of the diverse number of processing parameters that may be modified in order to reduce a scrap factor associated with the method 100 of the present invention. The adjustment and modification of various other processing parameters is intended to be included herewith as may be desired.

With reference to FIG. 5, it should be noted that one or more steps of the invention of the present method may be repeated or reiterated 140 as may be desired until a certain target or range may be achieved. Thus, it is possible to identify more than one scrap factor to be correlated against processing parameters in order to reduce more than one scrap factor in the total amount of scrap. In some instances, it may be undesirable to modify/adjust many processing parameters at a single time, as changing multiple variables at once may create other problems in manufacturing. For example, on a first pass through the method, a scrap for mixing may be reduced, while on subsequent passes, other scrap factors may be reduced. Thus, the method 100 may be evolving and improving, while the desirable parameters may be tracked or logged for use in other products. For example, certain processing parameters may be advantageous for processing films of one composition, but not as advantageous for processing films of a different compositional make-up, a different thickness, or differing in other physical or chemical properties. The particular adjustments made in the present method 100 are specific to the particular final dosage form desired, including the components and properties of the final dosage.

Similarly, it is possible to reduce the amount of scrap iteratively over a desired number of calculations (modeling the manufacturing process) or during one or more runs in order to continually achieve an improved result over previous runs. An example of this may include, for example, adjusting the coating width enough so that an edge trim may be employed to cut off any non-uniform edges along the film sheet, where the edge trim is limited to only non-uniform film material, and no uniform film product is sacrificed to the scrap for cutting area.

One or more of the steps of the present method may be completed throughout the manufacturing process in order to ensure that desirable film products are produced. Thus, the method may be completed in-line as the film is being manufactured and produced, or with real-time measurements taken, to be determined, correlated, and adjusted in accordance with the method 100. Alternatively, the method 100 may be completed as a modeling process prior to manufacture in order to plan efficient process design for various final film products. The method 100 may also be completed prior to initializing the manufacturing as a calibration or quality control step to ensure the most efficient and economical usage of actives and ingredients in the film. The method 100 may be completed at the end of a run, either to aid in the diagnosis or trouble shooting of unknown problems or errors, or to supplement other measurements with respect to the manufacturing specifications and parameters. One or more steps of the method 100 may be completed through iterative calculations, comparisons, or through the aid of a computer system 150, shown for example, in FIG. 5A.

The present invention may further comprise a system for optimizing the production of self-supporting film. The system includes a manufacturing apparatus for a film product, and a computer system 150, which may run the method 100 with respect to the process design of the manufacturing system.

The manufacturing apparatus may include one or more of the instruments and equipment discussed supra. For example, the manufacturing equipment of the system may include a mixer, a film former, a drying apparatus, and a cutting apparatus, as well as all intervening components. As further examples of the manufacturing equipment that may be used in the present invention: the mixer may desirably include a mother/daughter mixer; the film former may desirably include a reverse roll coating apparatus; the drying apparatus may desirably include an oven; and the cutting apparatus may desirably include a slitter and/or a packaging machine.

The computer system 150 may execute the method 100, including tracking of processing parameters and scrap produced in a system of optimizing self-supporting film production. The computer system 150 may be generally defined by the elements included in the block diagram of FIG. 5A.

The computer system 150 may be integral to the manufacturing equipment or remotely associated to the manufacturing equipment through wireless connections or remote data entry. The computer system 150 may constantly (or intermittently) acquire various data from the manufacturing system, taking readings of the various processing parameters, scrap factors, and the like. The computer system 150 may monitor at least one product characteristic to further provide information on whether a final product with desirable characteristics is achieved. The computer system 150 may control at least one processing parameter in order to promote the production of a desirable final product and an efficient process (with reduced total scrap).

The system 150 may be adjustable in-line to comport with real-time processing and manufacture of film. It may also be desirable for the system 150 to include a film manufacturing apparatus which may be remotely adjustable.

Figure 5A:
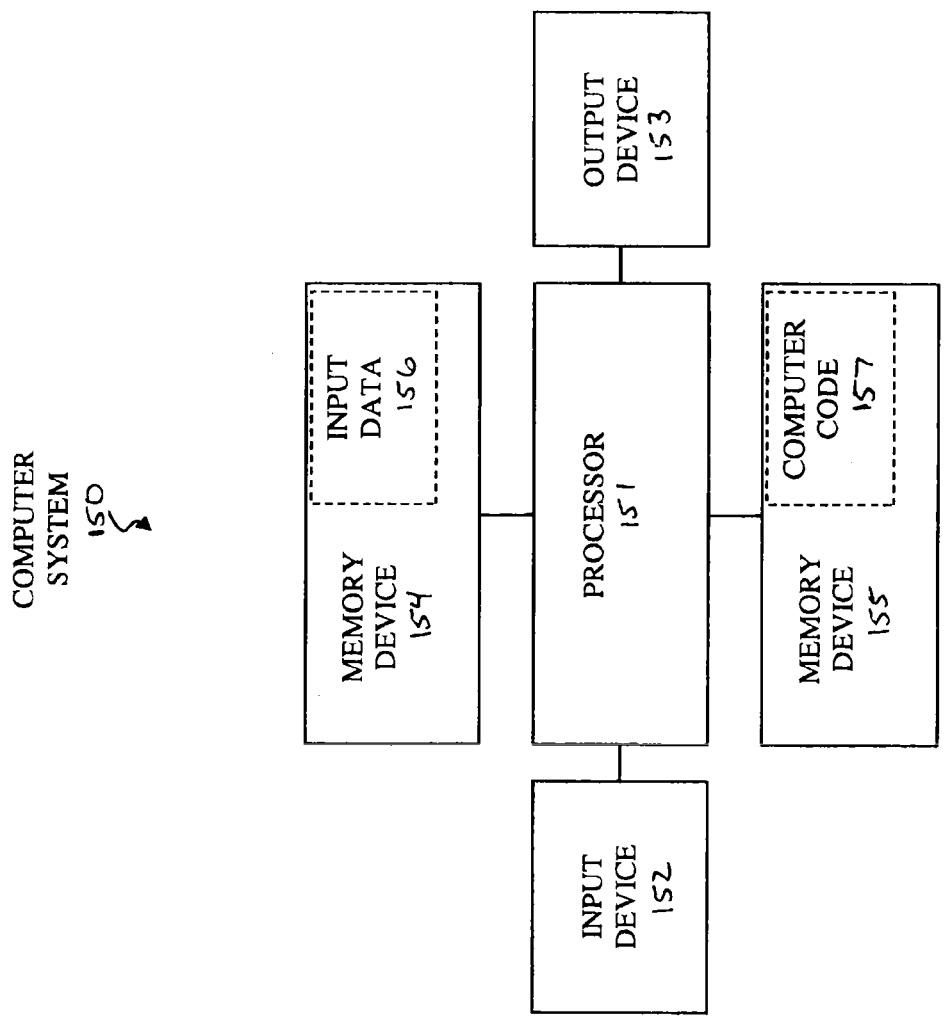
FIG. 5A is a block diagram, which depicts a computer system, which may be employed with the embodiments of the present invention.

The system 150 of FIG. 5A may be used for optimizing a method of film production 100, in accordance with method 100 and system of the present invention. In one embodiment, the computer system 150 may include a processor 151, an input device 152 coupled to the processor 151, an output device 153 coupled to the processor 151, and one or more memory devices 154 and 155 each coupled to the processor 151.

The processor 151 performs computation and control functions of computing unit or computer system 150, and may include a single processing unit, or may be distributed across one or more processing units in one or more locations.

The input device 152 may be, inter alia, a keyboard, a mouse, a keypad, a touchscreen, a voice recognition device, a sensor, a network interface card (NIC), a Voice/video over Internet Protocol (VOIP) adapter, a wireless adapter, a telephone adapter, a dedicated circuit adapter, etc.

The output device 153 may be, inter alia, a printer, a plotter, a computer screen, a magnetic tape, a removable hard disk, a floppy disk, a NIC, a VOIP adapter, a wireless adapter, a telephone adapter, a dedicated circuit adapter, an audio and/or visual signal generator, a light emitting diode (LED), and the like.

The memory devices 154 and 155 may be, inter alia, a cache, a dynamic random access memory (DRAM), a read-only memory (ROM), a hard disk, a floppy disk, a magnetic tape, an optical storage such as a compact disk (CD) or a digital video disk (DVD), etc. The memory device 155 preferably includes a computer code 157, which is a computer program that comprises computer-executable instructions. The computer code 157 may include, inter alia, an algorithm used for utilizing generational file names according to the present invention.

Memory may comprise any known type of data storage and/or transmission media, including bulk storage, magnetic media, optical media, random access memory (RAM), read-only memory (ROM), a data cache, a data object, and the like. Cache memory elements provide temporary storage of at least some program code in order to reduce the number of times code must be retrieved from bulk storage during execution. The storage unit is, for example, a magnetic disk drive or an optical disk drive that stores data. Moreover, similar to processor 151, memory may reside at a single physical location, comprising one or more types of data storage, or be distributed across a plurality of physical systems in various forms. Further, memory can include data distributed across, for example, a LAN, WAN or storage area network (SAN) (not shown).

The processor 151 executes the computer code 157. The memory device 154 includes input data 156. The input data 156 includes input required by the computer code 157. The output device 153 displays output from the computer code 157. Either or both memory devices 154 and 155 (or one or more additional memory devices not shown in FIG. 5A) may be used as a computer usable storage medium (or a computer readable storage medium or a program storage device) having a computer readable program embodied therein and/or having other data stored therein. The computer readable program comprises the computer code 157. Generally, a computer program product (or, alternatively, an article of manufacture) of the computer system 150 may include computer usable storage medium (or program storage device).

While FIG. 5A shows the computer system 150 as a particular configuration of hardware and software, any configuration of hardware and software may be utilized for the purposes in conjunction with the particular computer system 150 of FIG. 5A, as may be desired. For example, the memory devices 154 and 155 may be portions of a single memory device rather than separate memory devices.

The computer system 150 can take the form of an entirely hardware embodiment, an entirely software embodiment or an embodiment containing both hardware and software elements. In a preferred embodiment, the invention may be implemented in software. Furthermore, the computer system 150 can take the form of a computer program product accessible from a computer-usable or computer-readable medium providing program code for use-by or in-connection with a computing system or any instruction execution system to provide and facilitate the capabilities of the present invention. For the purposes of this description, a computer-usable or computer-readable medium can be any apparatus that can contain, store, communicate, propagate, or transport the program for use by or in connection with the instruction execution system, apparatus, or device.

EXAMPLES

Example I

Correlating Lost Coating to the Tank Size

Figure 6:
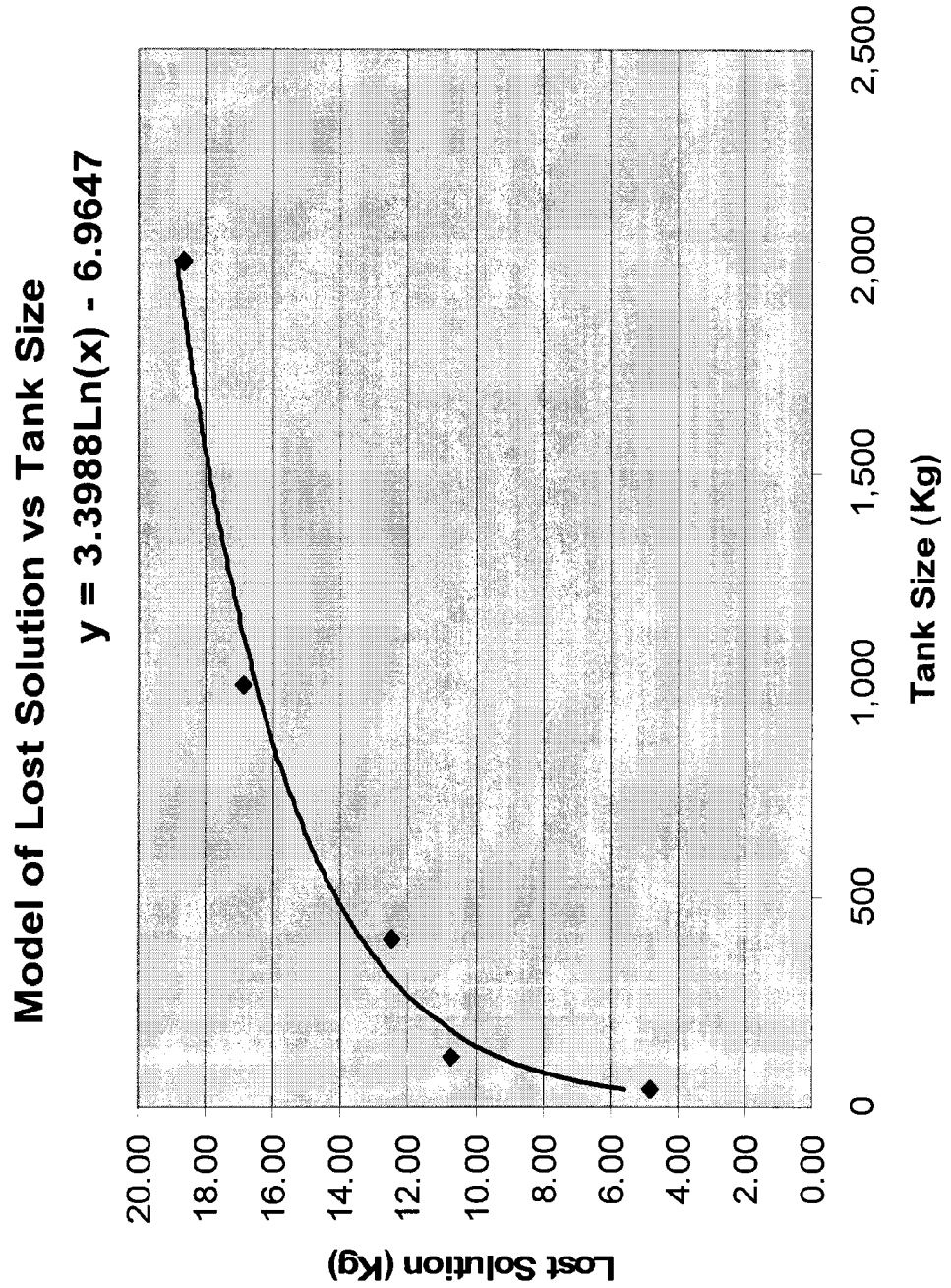
FIG. 6 is a chart of experimental data, which depicts the trend between the coating lost to the hoses and tanks as a function of the total batch size.

In order to understand the coating lost to the mixer and hoses, 192 runs on various sized tanks were completed. The amount of coating solution lost was tabulated for each run. Then, average solution lost was computed for each tank size over the total number of runs reviewed. Below is a listing of the data from the 192 runs at tank sizes including 40 liter, 120 liter, 400 liter, 1,000 liter and 2,000 liter The trend of tank size versus solution lost is depicted in FIG. 6, which correlates the trend observed from the data into the formula: $y=3.3988 \, Ln(x)-6.9467$, where y includes the coating lost to hoses and tank surfaces, and x includes the tank size.

The average mixing losses, which are depicted on FIG. 6, are set forth in Table II below:

TABLE II

| Mixer Losses (kg) | |
| --- | --- |
| Tank size (liters) | Average solution lost (kg) |
| 40 | 4.83 |
| 120 | 10.76 |
| 400 | 12.49 |
| 1000 | 16.91 |
| 1,2000 | 18.67 |

Seventeen runs were completed on a 40 liter Tank. Table III below depicts the total batch size (kg) and the total solution lost to the mixer and hoses (kg).

TABLE III

| Run No. | Batch size | Kg lost |
| --- | --- | --- |
| 1 | 38 | 3.02 |
| 2 | 38 | 3.26 |
| 3 | 38 | 3.58 |
| 4 | 38 | 3.95 |
| 5 | 38 | 4.01 |
| 6 | 38 | 4.15 |
| 7 | 38 | 4.17 |
| 8 | 38 | 4.20 |
| 9 | 38 | 4.30 |
| 10 | 38 | 4.30 |
| 11 | 38 | 4.70 |
| 12 | 38 | 5.30 |
| 13 | 38 | 5.30 |
| 14 | 38 | 5.50 |

TABLE III-continued

| Run No. | Batch size | Kg lost |
|---|---|---|
| 15 | 38 | 5.62 |
| 16 | 38 | 7.71 |
| 17 | 41 | 9.03 |

Forty-one runs were then completed on a 120 liter Tank. Table IV below depicts the total batch size (kg) and the total solution lost to the mixer and hoses (kg).

TABLE IV

| Run No. | Batch size | Kg lost |
|---|---|---|
| 1 | 80 | 28.00 |
| 2 | 101 | 2.10 |
| 3 | 101 | 23.40 |
| 4 | 115 | 4.60 |
| 5 | 115 | 4.60 |
| 6 | 115 | 5.10 |
| 7 | 115 | 5.50 |
| 8 | 115 | 6.08 |
| 9 | 115 | 7.00 |
| 10 | 115 | 7.10 |
| 11 | 115 | 7.40 |
| 12 | 115 | 8.00 |
| 13 | 115 | 8.40 |
| 14 | 115 | 9.20 |
| 15 | 115 | 9.30 |
| 16 | 115 | 9.30 |
| 17 | 115 | 9.30 |
| 18 | 115 | 9.30 |
| 19 | 115 | 9.30 |
| 20 | 115 | 9.30 |
| 21 | 115 | 9.60 |
| 22 | 115 | 9.60 |
| 23 | 115 | 9.60 |
| 24 | 115 | 9.60 |
| 25 | 115 | 9.90 |
| 26 | 115 | 10.20 |
| 27 | 115 | 10.60 |
| 28 | 115 | 11.20 |
| 29 | 115 | 11.30 |
| 30 | 115 | 11.50 |
| 31 | 115 | 11.80 |
| 32 | 115 | 12.20 |
| 33 | 115 | 12.20 |
| 34 | 115 | 12.20 |
| 35 | 115 | 12.20 |
| 36 | 115 | 12.70 |
| 37 | 115 | 14.70 |
| 38 | 115 | 17.40 |
| 39 | 115 | 17.90 |
| 40 | 115 | 29.60 |
| 41 | 121 | 2.94 |

Seventy runs were then completed on a 400 liter Tank. Table V below depicts the total batch size (kg) and the total solution lost to the mixer and hoses (kg).

TABLE V

| Run No. | Batch size | Kg lost |
|---|---|---|
| 1 | 205 | 8.30 |
| 2 | 227 | 5.30 |
| 3 | 227. | 13.90 |
| 4 | 227. | 16.70 |
| 5 | 250 | 8.40 |
| 6 | 250 | 8.70 |
| 7 | 250 | 9.40 |
| 8 | 250 | 9.50 |
| 9 | 250 | 9.50 |
| 10 | 250 | 10.80 |
| 11 | 250 | 10.80 |
| 12 | 250 | 12.00 |
| 13 | 250 | 13.10 |
| 14 | 250 | 14.40 |
| 15 | 250 | 14.90 |
| 16 | 250 | 15.00 |
| 17 | 250 | 17.90 |
| 18 | 250 | 20.10 |
| 19 | 265 | 9.30 |
| 20 | 265 | 9.60 |
| 21 | 265 | 9.60 |
| 22 | 265 | 9.90 |
| 23 | 265 | 9.90 |
| 24 | 265 | 10.00 |
| 25 | 265 | 10.00 |
| 26 | 265 | 10.20 |
| 27 | 265 | 10.50 |
| 28 | 265 | 10.89 |
| 29 | 265 | 10.89 |
| 30 | 265 | 12.00 |
| 31 | 265 | 12.00 |
| 32 | 265 | 14.20 |
| 33 | 265 | 17.45 |
| 34 | 265 | 19.30 |
| 35 | 275 | 4.62 |
| 36 | 280 | 3.10 |
| 37 | 280 | 4.09 |
| 38 | 280 | 6.30 |
| 39 | 280 | 6.80 |
| 40 | 280 | 7.30 |
| 41 | 280 | 7.90 |
| 42 | 280 | 8.40 |
| 43 | 280 | 8.40 |
| 44 | 280 | 8.70 |
| 45 | 280 | 10.70 |
| 46 | 280 | 11.50 |
| 47 | 280 | 11.90 |
| 48 | 280 | 11.90 |
| 49 | 280 | 12.00 |
| 50 | 280 | 12.00 |
| 51 | 280 | 12.30 |
| 52 | 280 | 12.90 |
| 53 | 280 | 13.90 |
| 54 | 280 | 14.00 |
| 55 | 280 | 15.10 |
| 56 | 280 | 15.70 |
| 57 | 280 | 17.00 |
| 58 | 280 | 17.90 |
| 59 | 280 | 19.00 |
| 60 | 280 | 23.90 |
| 61 | 280 | 24.40 |
| 62 | 380 | 11.93 |
| 63 | 380 | 11.93 |
| 64 | 380 | 12.00 |
| 65 | 380 | 12.00 |
| 66 | 380 | 17.70 |
| 67 | 380 | 17.70 |
| 68 | 380 | 18.30 |
| 69 | 380 | 23.40 |
| 70 | 380 | 23.40 |

Fifty-four runs were completed on a 1000 liter Tank. Table VI below depicts the total batch size (kg) and the total solution lost to the mixer and hoses (kg).

TABLE VI

| Run No. | Batch size | Kg lost |
|---|---|---|
| 1 | 850 | 9.00 |
| 2 | 850 | 11.20 |
| 3 | 850 | 11.30 |
| 4 | 850 | 12.00 |
| 5 | 850 | 12.00 |
| 6 | 850 | 12.00 |
| 7 | 850 | 12.00 |
| 8 | 850 | 12.00 |
| 9 | 850 | 12.00 |

TABLE VI-continued

| Run No. | Batch size | Kg lost |
|---|---|---|
| 10 | 850 | 12.00 |
| 11 | 850 | 12.00 |
| 12 | 850 | 12.00 |
| 13 | 850 | 12.00 |
| 14 | 850 | 13.10 |
| 15 | 850 | 13.69 |
| 16 | 850 | 13.69 |
| 17 | 850 | 13.80 |
| 18 | 850 | 13.80 |
| 19 | 850 | 15.20 |
| 20 | 850 | 15.70 |
| 21 | 850 | 15.70 |
| 22 | 850 | 17.30 |
| 23 | 850 | 17.90 |
| 24 | 850 | 18.00 |
| 25 | 850 | 18.80 |
| 26 | 850 | 19.10 |
| 27 | 850 | 20.20 |
| 28 | 850 | 20.20 |
| 29 | 850 | 20.50 |
| 30 | 850 | 20.50 |
| 31 | 850 | 21.60 |
| 32 | 850 | 21.60 |
| 33 | 850 | 23.20 |
| 34 | 850 | 23.20 |
| 35 | 850 | 23.90 |
| 36 | 850 | 23.90 |
| 37 | 850 | 25.40 |
| 38 | 850 | 28.12 |
| 39 | 850 | 28.12 |
| 40 | 850 | 38.80 |
| 41 | 950 | 9.00 |
| 42 | 950 | 10.60 |
| 43 | 950 | 11.20 |
| 44 | 950 | 11.70 |
| 45 | 950 | 12.00 |
| 46 | 950 | 12.00 |
| 47 | 950 | 12.00 |
| 48 | 950 | 12.00 |
| 49 | 950 | 12.00 |
| 50 | 950 | 15.30 |
| 51 | 950 | 17.70 |
| 52 | 950 | 22.00 |
| 53 | 950 | 28.00 |
| 54 | 950 | 31.20 |

Nine runs were completed on a 2000 liter Tank. Table VII below depicts the total batch size (kg) and the total solution lost to the mixer and hoses (kg).

TABLE VII

| Run No. | Batch size | Kg lost |
|---|---|---|
| 1 | 1,380 | 12 |
| 2 | 1,380 | 12 |
| 3 | 1,380 | 12 |
| 4 | 1,700 | 12 |
| 5 | 1,900 | 24 |
| 6 | 1,900 | 24 |
| 7 | 1,900 | 24 |
| 8 | 1,900 | 24 |
| 9 | 1,900 | 24 |

To determine mixer loses, data was compiled from the above 192 batches. Lost solution was determined to be a function of tank size. Thus, even if a mixer is run at half capacity (i.e. half full), the same total solution is lost (Lost Solution) in the pumps and hoses of the process. The resulting function of these batches, plotted on a chart of tank size (in kg) by mixer losses (in kg) is the relationship depicted in FIG. 6. The scrap for mixing refers to the amount of solution that is lost to hoses and mixer.

The scrap for mixing may be further defined by the formula (eq. 13):

$$M_{LM}(Kg) = (3.4031\, Ln(V_M(Kg))) - 6.8207 \qquad (eq.\ 13)$$

As explained above, other scrap associated with mixing, includes errors such as spills, equipment failures and other processing issues. This other error-based scrap is not a function of batch size or coating width, but tends to be more or less random and is therefore not considered in this optimization method.

Example II

Determining Coating Losses as Related to Start-up/Shut-down

In order to understand the coating losses which are attributed to the start-up and shut-down of the oven/drying process, the amount of coated solution lost was tabulated over 206 runs. As scrap in some of these runs was high as a result of one time anomalies, one hundred of the most ideal runs (lowest scrap) lots were used as examples for this calculation. Efficiency in the start-up and shut-down is an area in which constant efforts are made to improve. The amount of scrap film was tracked for each run. "Scrap film" refers to that film which did not have the proper uniformity/consistency upon the completion of the drying process, thus it was discarded. For the runs in this Example, the oven length was a standard length of 9 m. The average total scrap for each run was 87 m, regardless of the batch size. Thus, 87 m of scrap, divided by 9 m of oven length is 9.7, which is the coefficient of equation 5 (eq. 5), a variable in the determination of Scrap for Coating. That is, regardless of the batch size, the average loss for start-up/shut-down was determined to be 87 meters in length, which is 9.7 times the oven length. Currently 9 meters, this length is the amount of material that must typically be run through the oven to be initialized before the end film sheet product has the most desirable characteristics obtained. Thus, the amount of scrap for coating is also a direct function of the coating width selected. While the coating width is minimized, the start up/shut down scrap will also be minimized.

The scrap for coating may be defined by the formula:

$$C_{SS}(m^2) = 9.7 * L_O(m) * W_C(m) \qquad (eq.\ 5)$$

It is noted that 9.7 is the coefficient generated from the analysis of a select 100 runs (set forth below in Table VIII). To determine the coating losses at start-up and shut down of the process, the average of the best 100 runs were used. This average is in accordance with the results that are accomplished on a routine basis. The average loss of coating from these 100 runs was 87 meters. It is understood that this coefficient can vary with different formulations and different drying ovens, and will need to be evaluated for any specific product. The "% coating scrap" is defined by the scrap for coating (m²) divided by the total square meters of film produced times 100.

There can be other scrap associated with coating, i.e. web breaks, equipment failures and other processing issues. This scrap is not a function of batch size or coating width, but tends to be more or less random and is therefore not considered in this optimization method.

The term "oven length" generally refers to the total length under which moisture and/or water is removed from the wet film or cast film, before the film is completed into the final film product or film sheet product. The oven length was 9 meters for these 100 runs.

TABLE VIII

| Run No. | Scrap (M) | Batch size (kg) |
|---|---|---|
| 1 | 38.7 | 265 |
| 2 | 38.7 | 265 |
| 3 | 39.7 | 265 |
| 4 | 41.1 | 265 |
| 5 | 41.1 | 265 |
| 6 | 43.2 | 38 |
| 7 | 43.2 | 38 |
| 8 | 44.2 | 38 |
| 9 | 44.2 | 38 |
| 10 | 44.3 | 115 |
| 11 | 44.3 | 115 |
| 12 | 44.3 | 115 |
| 13 | 44.3 | 115 |
| 14 | 47.0 | 280 |
| 15 | 50.5 | 38 |
| 16 | 50.6 | 41 |
| 17 | 57.3 | 38 |
| 18 | 58.3 | 38 |
| 19 | 58.7 | 38 |
| 20 | 59.9 | 280 |
| 21 | 63.8 | 280 |
| 22 | 64.3 | 38 |
| 23 | 64.9 | 265 |
| 24 | 64.9 | 265 |
| 25 | 65.0 | 115 |
| 26 | 65.3 | 280 |
| 27 | 65.9 | 115 |
| 28 | 65.9 | 115 |
| 29 | 65.9 | 115 |
| 30 | 65.9 | 115 |
| 31 | 70.2 | 280 |
| 32 | 71.1 | 280 |
| 33 | 72.3 | 115 |
| 34 | 72.3 | 115 |
| 35 | 72.3 | 115 |
| 36 | 72.3 | 115 |
| 37 | 72.4 | 265 |
| 38 | 72.4 | 265 |
| 39 | 72.7 | 115 |
| 40 | 72.9 | 115 |
| 41 | 72.9 | 115 |
| 42 | 73.7 | 280 |
| 43 | 73.9 | 101 |
| 44 | 74.4 | 38 |
| 45 | 75.3 | 265 |
| 46 | 75.4 | 115 |
| 47 | 77.8 | 280 |
| 48 | 79.9 | 115 |
| 49 | 81.2 | 265 |
| 50 | 82.5 | 280 |
| 51 | 84.0 | 250 |
| 52 | 86.8 | 280 |
| 53 | 87.3 | 280 |
| 54 | 90.3 | 275 |
| 55 | 90.5 | 227 |
| 56 | 90.9 | 280 |
| 57 | 92.3 | 250 |
| 58 | 92.5 | 115 |
| 59 | 94.5 | 280 |
| 60 | 95.4 | 265 |
| 61 | 96.8 | 380 |
| 62 | 96.8 | 380 |
| 63 | 97.1 | 38 |
| 64 | 97.5 | 38 |
| 65 | 97.6 | 250 |
| 66 | 98.6 | 250 |
| 67 | 98.7 | 280 |
| 68 | 99.6 | 280 |
| 69 | 99.8 | 115 |
| 70 | 102.0 | 280 |
| 71 | 104.0 | 115 |
| 72 | 104.2 | 38 |
| 73 | 108.6 | 115 |
| 74 | 110.6 | 38 |
| 75 | 113.3 | 280 |
| 76 | 115.4 | 250 |
| 77 | 115.8 | 280 |
| 78 | 115.8 | 115 |
| 79 | 116.8 | 280 |
| 80 | 119.6 | 115 |
| 81 | 121.7 | 250 |
| 82 | 122.4 | 115 |
| 83 | 122.8 | 850 |
| 84 | 122.9 | 250 |
| 85 | 124.2 | 115 |
| 86 | 124.5 | 250 |
| 87 | 127.2 | 850 |
| 88 | 128.5 | 850 |
| 89 | 129.0 | 280 |
| 90 | 130.1 | 850 |
| 91 | 130.2 | 280 |
| 92 | 130.6 | 38 |
| 93 | 132.9 | 380 |
| 94 | 132.9 | 380 |
| 95 | 137.0 | 250 |
| 96 | 144.8 | 280 |
| 97 | 144.9 | 280 |
| 98 | 145.3 | 250 |
| 99 | 149.3 | 115 |
| 100 | 152.9 | 280 |

Example III

Exemplary Film or Sheet Process with Exemplary Scrap

Table IX below depicts, for tank sizes of 40 liter, 120 liter, 400 liter, 1000 liter and 2000 liter, the possible results of a batch of solution, which is coated, dried, cut and packaged. The film manufacturing process along these metrics has scrap computed for it, including a scrap for mixing, a scrap for coating, a scrap for slitting and a scrap for packaging. For the purposes of this example, the optimum coating width discussed above was used.

TABLE IX

| | | | | | |
|---|---|---|---|---|---|
| Tank Size (liters) | 40 | 100 | 400 | 1000 | 2000 |
| Total Batch wt (kg) | 38 | 115 | 380 | 950 | 1900 |
| Theoretical Strips | 152,000 | 460,000 | 1,520,000 | 3,800,000 | 7,600,000 |
| strips to coater | 129,767 | 422,693 | 1,466,423 | 3,733,950 | 7,524,515 |
| % Mixing Scrap | 14.6% | 8.1% | 3.5% | 1.7% | 1.0% |
| strips to slitter | 99,742 | 359,155 | 1,344,932 | 3,514,856 | 7,181,920 |
| % Coating scrap | 19.8% | 13.8% | 8.0% | 5.8% | 4.5% |
| strips to packaging | 92,101 | 344,761 | 1,311,369 | 3,451,292 | 7,057,676 |
| % Slitting Scrap | 5.0% | 3.1% | 2.2% | 1.7% | 1.6% |
| total packaged strips | 82,123 | 317,778 | 1,219,331 | 3,215,231 | 6,578,897 |
| % Packaging Scrap | 6.6% | 5.9% | 6.1% | 6.2% | 6.3% |
| % total scrap | 46% | 31% | 20% | 15% | 13% |

Example IV

Impact of Batch Size on Scrap

Figure 7:
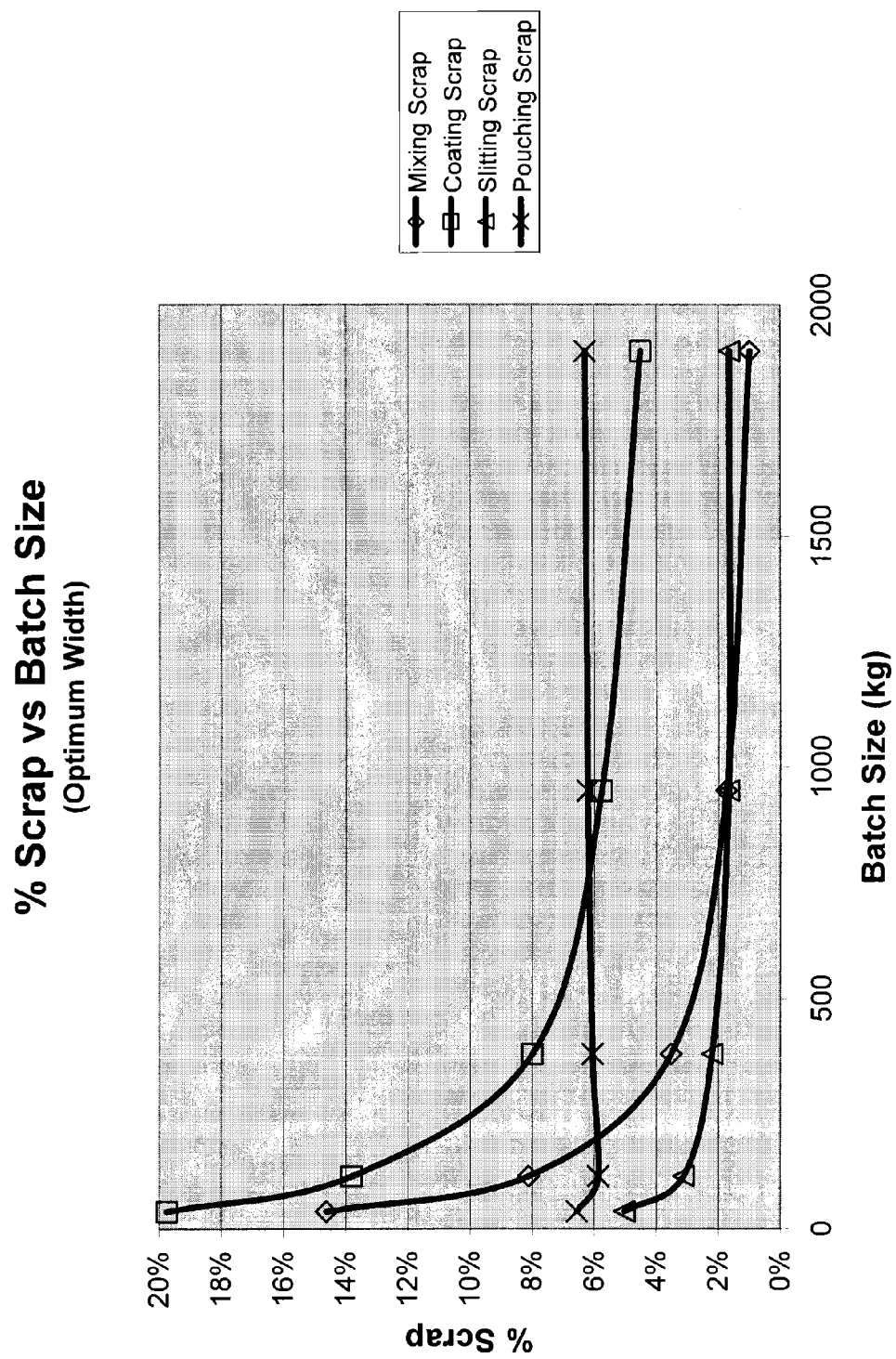
FIG. 7 is a chart depicting the % scrap associated with each manufacturing step as a function of batch size.

Using the data from Example III above, one can evaluate the relationship between batch size and the four main types of scrap. This data is represented in FIG. 7. The results of this data indicate the following:

Mixing Scrap is a strong function of Batch size; Coating Scrap is a strong function of Batch size; Slitting Scrap is a moderate function of Batch size; and Packaging Scrap is a minimal function of Batch size.

With reference to FIG. 7, the percentage of scrap is depicted with use of an optimum width. The percentage of scrap is depicted with respect to the batch size in kg. The optimum coating width refers to the width that will yield the least amount of scrap for a given batch size.

Figure 8:
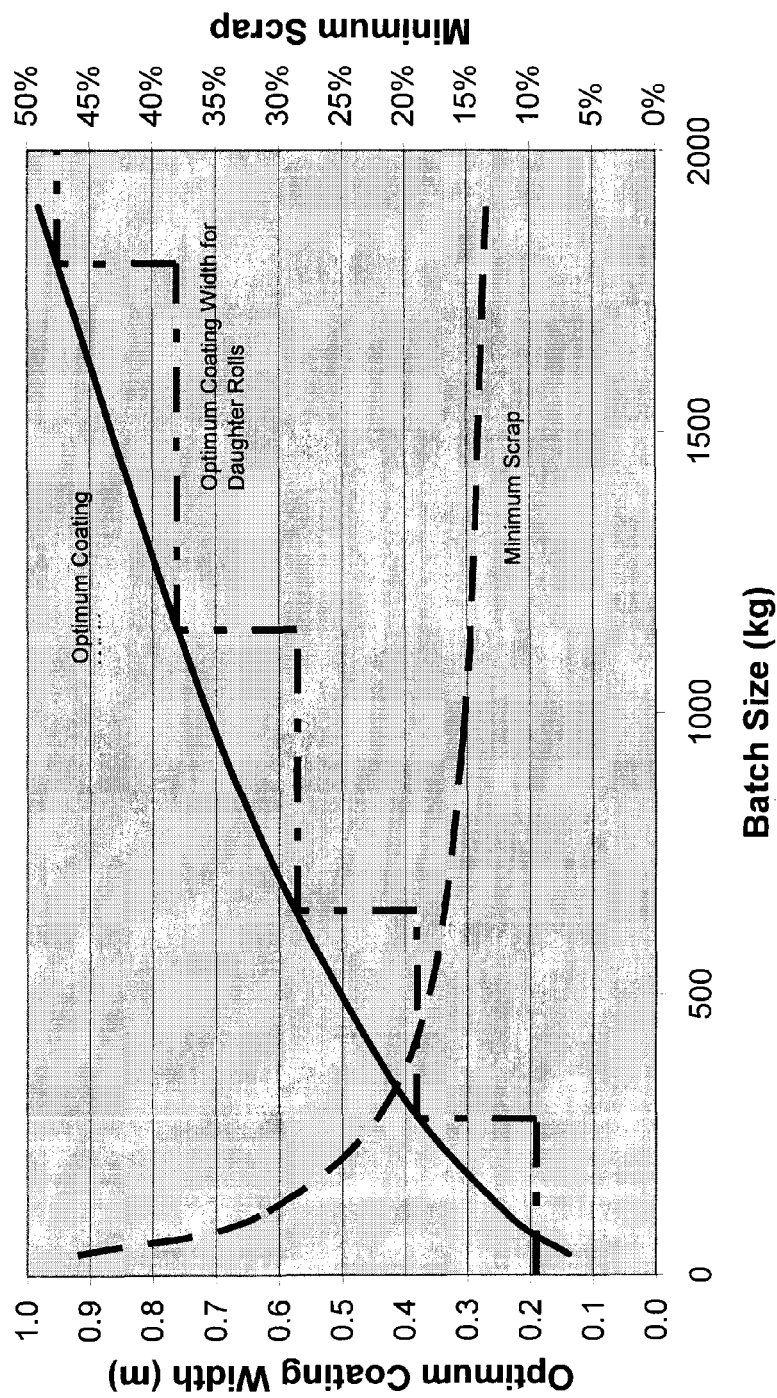
FIG. 8 is a chart depicting the optimum coating width and minimum scrap as a function of batch size.

FIG. 8 depicts the optimum coating width and process scrap as a function of batch size. The curved solid line from left to right is optimum coating width where the master roll is slit into the final product width, while the stepped dashed line refers to the optimum width for products where the master roll is slit into daughter rolls for a 8 lane packaging machine and a product 22 mm wide. The curved dashed line represents the minimum amount of scrap that can be expected using the optimum width.

The data depicted on the graph of FIG. 8 is based on the film product that is formed, dried, cut, and then packaged on a pouching machine. Thus, it is possible to optimize the width of coating in order to minimize scrap. In the present system of manufacturing, there is both fixed scrap and variable scrap.

It should, of course, be noted that there may be waste or "scrap" attributable to other variables, including errors such as improper packaging, improper cutting, or improper compositional makeup of the film, or such other scrap may be due to volatiles, degradation of one or more actives, as well as standard errors including the calibration of the equipment and instruments. However, these "other" factors, which may attribute to scrap and error are desirably minimized, and are not the focus of the present invention. It is desirable that such "other" factors should be minimized as much as possible to optimize the final amount of usable film.

Example V

Mixing Scrap as a Function of Coating Width

Figure 9:
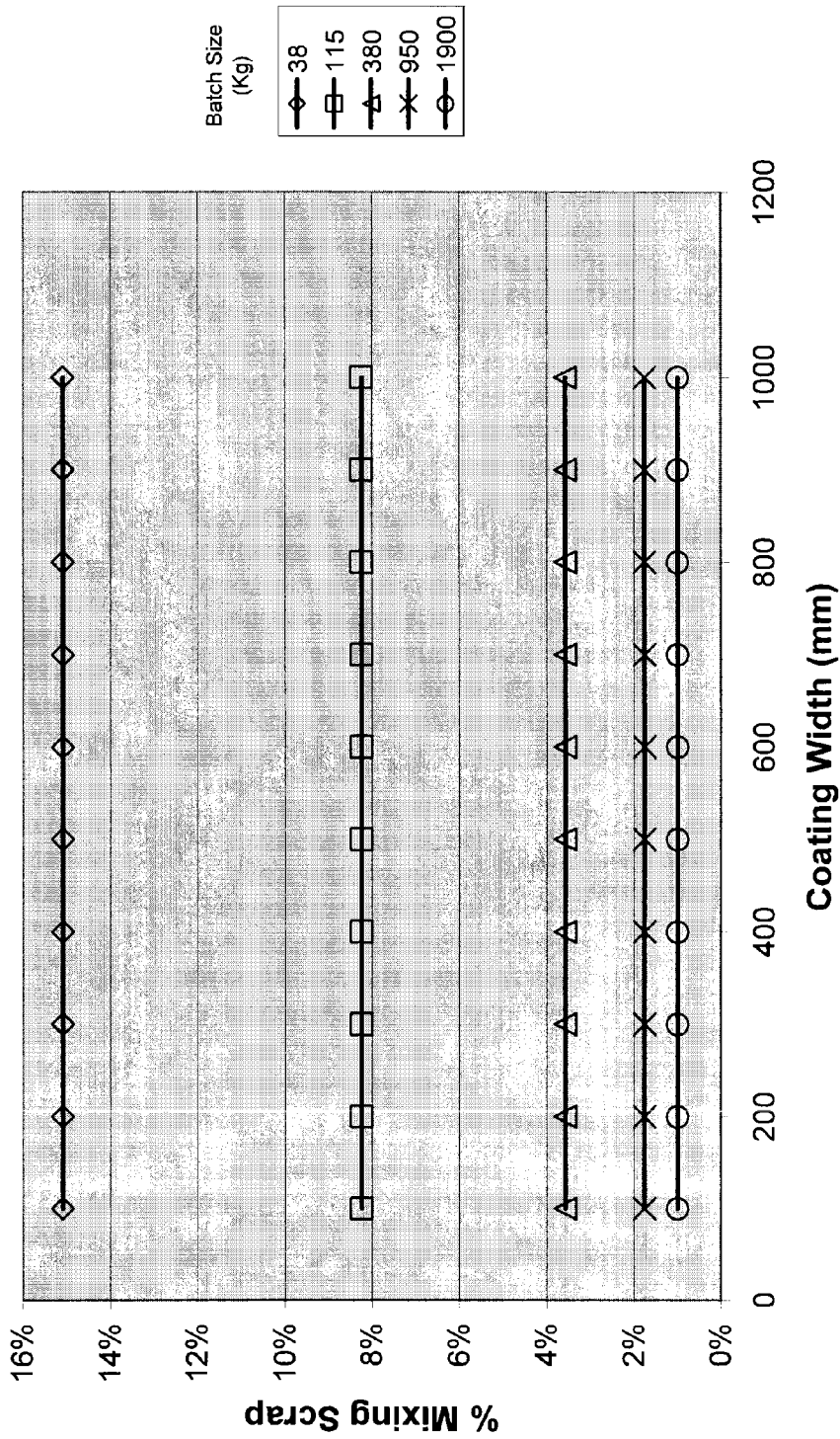
FIG. 9 is a chart depicting the mixing scrap as a function of coating width.

Using the methods set forth in the present application, one can evaluate the impact of coating width on Mixing Scrap for various Batch Sizes. This evaluation is shown in FIG. 9. As shown in FIG. 9, there appears to be minimal impact on the Mixing Scrap by changing the coating width.

Example VI

Coating Scrap as a Function of Coating Width

Figure 10:
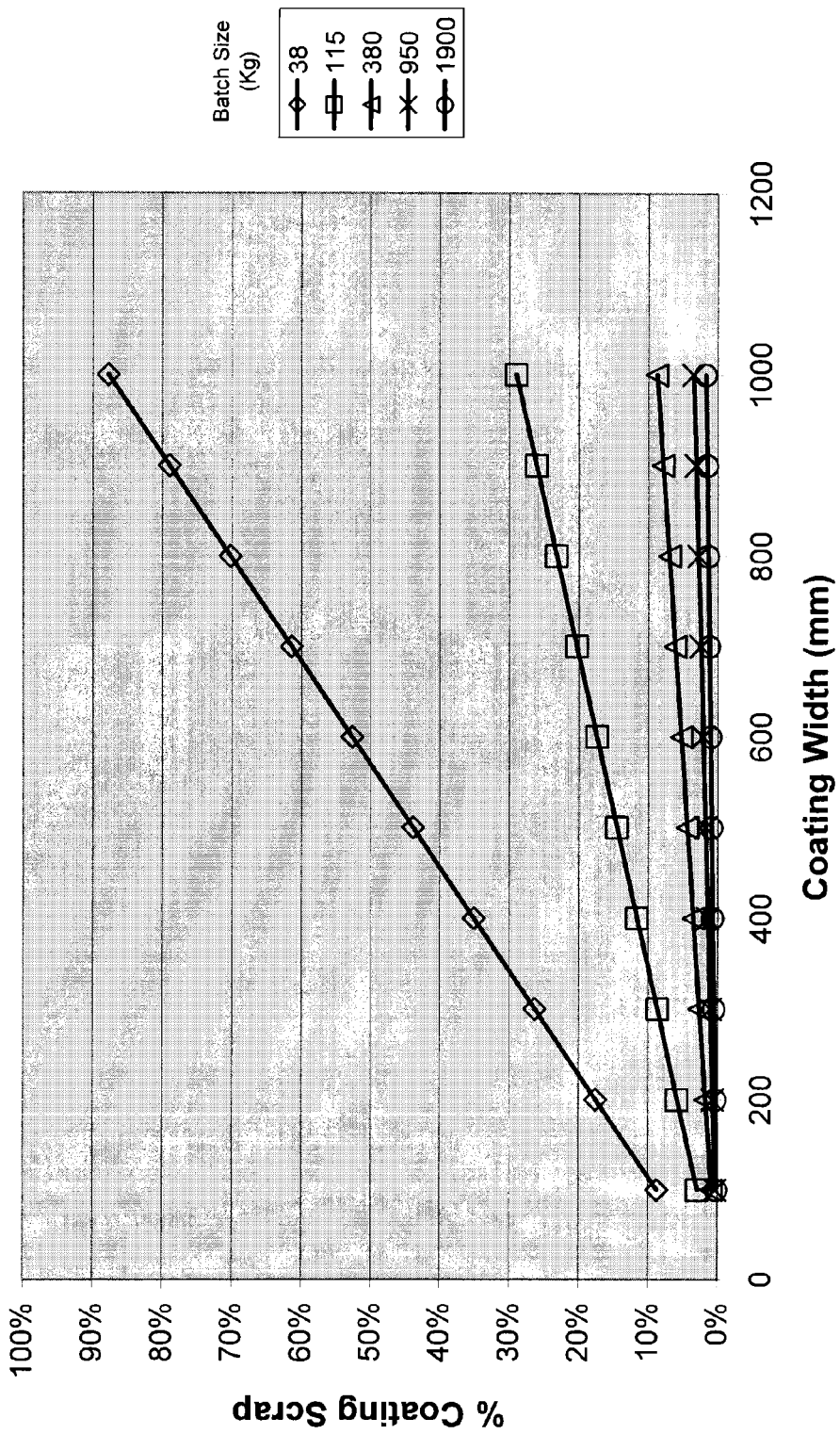
FIG. 10 is a chart depicting the coating scrap as a function of coating width.

Using the methods set forth in the present application, one can evaluate the impact of coating width on Coating Scrap for various Batch Sizes. This evaluation is shown in FIG. 10. As shown in FIG. 10, the following impact is observed. For all batch sizes, the relationship between Coating Scrap and Coating Width is linear, with the greater slop associated with the smaller batches.

Example VII

Slitting Scrap as a Function of Coating Width

Figure 11:
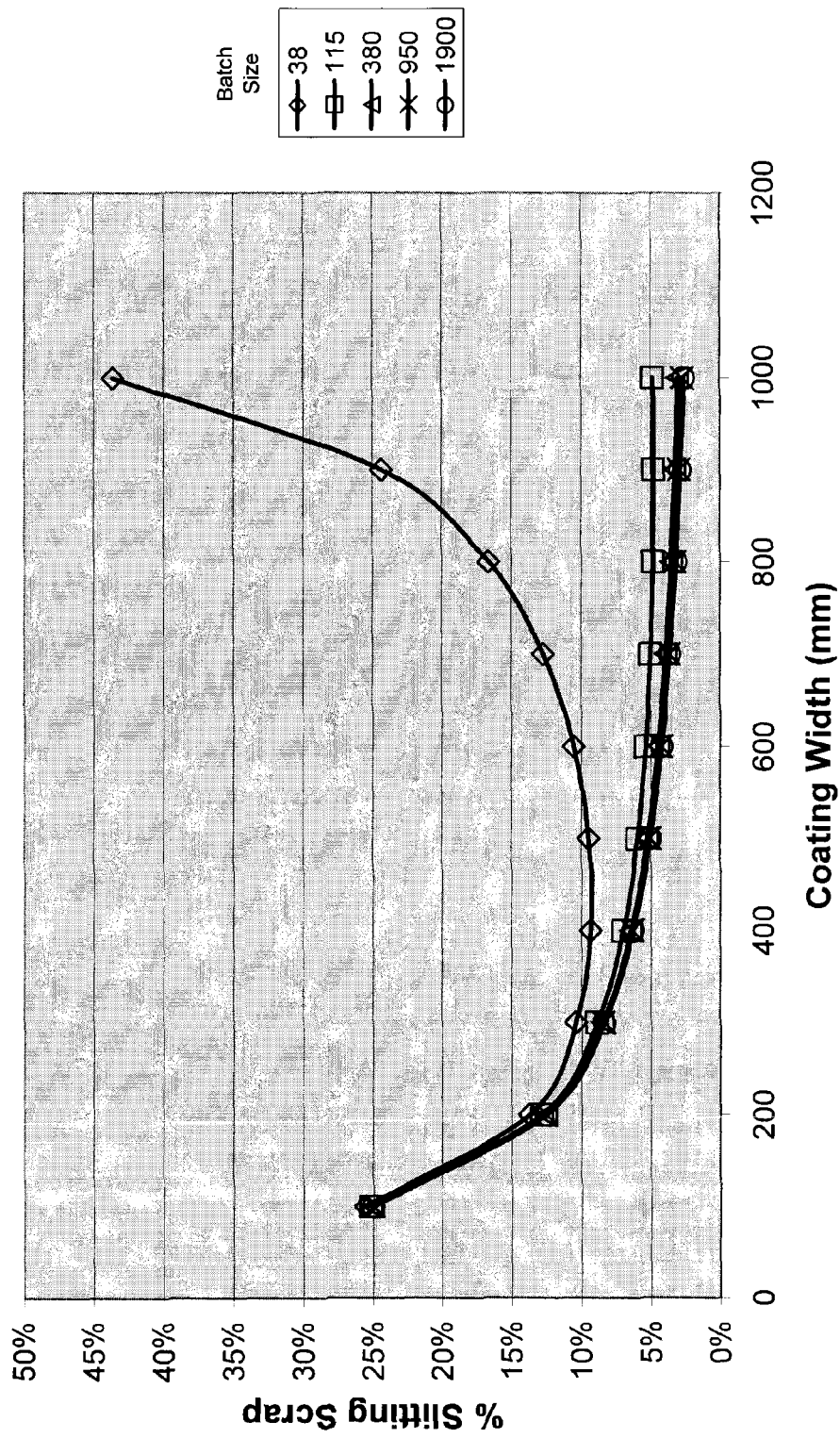
FIG. 11 is a chart depicting slitting scrap as a function of coating width.

Using the methods set forth in the present application, one can evaluate the impact of coating width on Slitting Scrap for various Batch Sizes. This evaluation is shown in FIG. 11. As shown in FIG. 11, there appears to be a strong inverse relationship between Slitting Scrap and Coating Width at the narrower widths, with much less of a correlation with batch size.

Example VIII

Packaging Scrap as a Function of Coating Width

Figure 12:
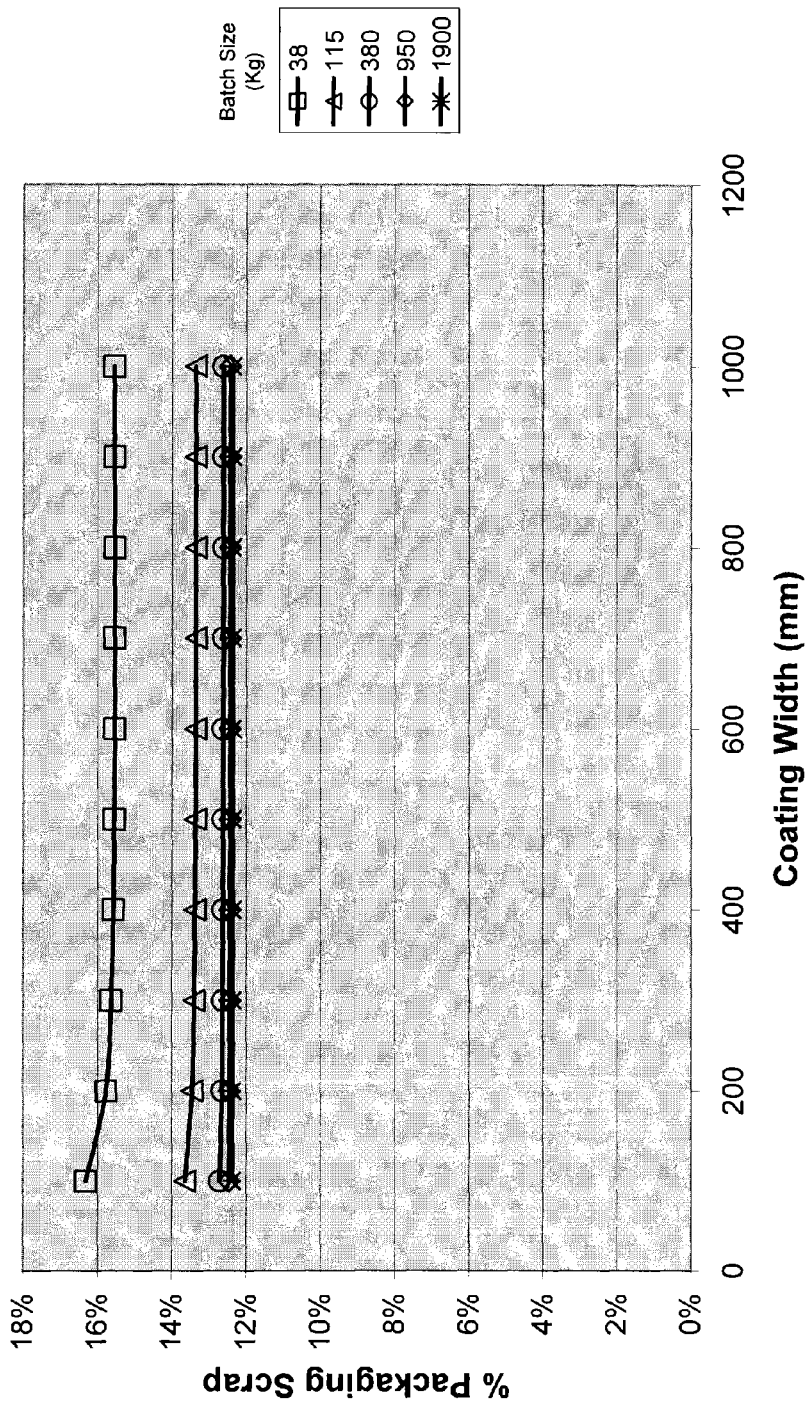
FIG. 12 is a chart depicting packaging scrap vs. coating width as a function of batch size.

Using the methods set forth in the present application, one can evaluate the impact of coating width on packaging scrap. This evaluation is shown in FIG. 12. FIG. 12 shows the predominately independent nature of the packaging scrap as a function of the coating width.

Example IX

Overall Scrap as a Function of Coating Width

Figure 13:
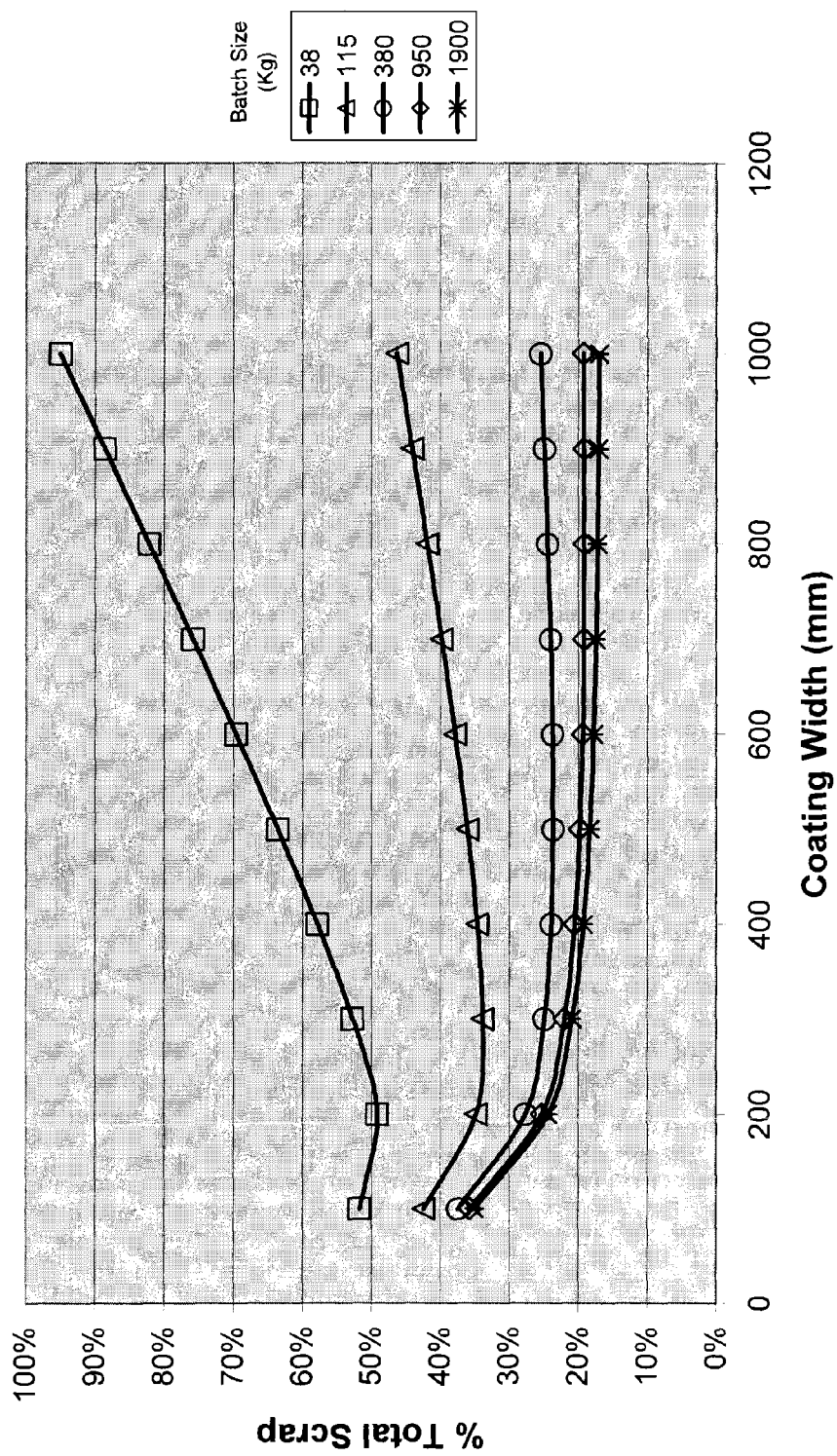
FIG. 13 is a chart depicting total scrap vs. coating width as a function of batch size.

Using the methods set forth in the present application, one can evaluate the impact of coating width on overall scrap. FIG. 13 shows the presence of an optimum width/minimum scrap for the smaller batch sizes.

Data for Examples IV-IX is set forth in the following table (Table X):

TABLE X

| Coating Width | Batch size | 100.0 | 200.0 | 300.0 | 400.0 | 500.0 | 600.0 | 700.0 | 800.0 | 900.0 | 1000.0 |
|---|---|---|---|---|---|---|---|---|---|---|---|
| % mixing loss | 38 | 15.1% | 15.1% | 15.1% | 15.1% | 15.1% | 15.1% | 15.1% | 15.1% | 15.1% | 15.1% |
| % mixing loss | 115 | 8.2% | 8.2% | 8.2% | 8.2% | 8.2% | 8.2% | 8.2% | 8.2% | 8.2% | 8.2% |
| % mixing loss | 380 | 3.6% | 3.6% | 3.6% | 3.6% | 3.6% | 3.6% | 3.6% | 3.6% | 3.6% | 3.6% |
| % mixing loss | 950 | 1.8% | 1.8% | 1.8% | 1.8% | 1.8% | 1.8% | 1.8% | 1.8% | 1.8% | 1.8% |
| % mixing loss | 1900 | 1.0% | 1.0% | 1.0% | 1.0% | 1.0% | 1.0% | 1.0% | 1.0% | 1.0% | 1.0% |
| % coating scrap | 38 | 8.8% | 17.5% | 26.3% | 35.1% | 43.9% | 52.6% | 61.4% | 70.2% | 79.0% | 87.7% |
| % coating scrap | 115 | 2.9% | 5.8% | 8.7% | 11.6% | 14.5% | 17.4% | 20.3% | 23.2% | 26.1% | 29.0% |
| % coating scrap | 380 | 0.9% | 1.8% | 2.6% | 3.5% | 4.4% | 5.3% | 6.1% | 7.0% | 7.9% | 8.8% |
| % coating scrap | 950 | 0.4% | 0.7% | 1.1% | 1.4% | 1.8% | 2.1% | 2.5% | 2.8% | 3.2% | 3.5% |
| % coating scrap | 1900 | 0.2% | 0.4% | 0.5% | 0.7% | 0.9% | 1.1% | 1.2% | 1.4% | 1.6% | 1.8% |
| % scrap slitting | 38 | 25.6% | 13.7% | 10.4% | 9.4% | 9.5% | 10.6% | 12.7% | 16.7% | 24.3% | 43.6% |
| % scrap slitting | 115 | 25.2% | 12.9% | 8.9% | 7.0% | 6.0% | 5.4% | 5.0% | 4.9% | 4.8% | 4.8% |
| % scrap slitting | 380 | 25.1% | 12.6% | 8.5% | 6.5% | 5.3% | 4.5% | 3.9% | 3.6% | 3.3% | 3.1% |
| % scrap slitting | 950 | 25.0% | 12.5% | 8.4% | 6.3% | 5.1% | 4.3% | 3.7% | 3.3% | 3.0% | 2.7% |
| % scrap slitting | 1900 | 25.0% | 12.5% | 8.4% | 6.3% | 5.1% | 4.2% | 3.6% | 3.2% | 2.9% | 2.6% |
| % packaging scrap | 38 | 16.3% | 15.8% | 15.6% | 15.6% | 15.5% | 15.5% | 15.5% | 15.5% | 15.5% | 15.6% |

TABLE X-continued

| Coating Width | Batch size | 100.0 | 200.0 | 300.0 | 400.0 | 500.0 | 600.0 | 700.0 | 800.0 | 900.0 | 1000.0 |
|---|---|---|---|---|---|---|---|---|---|---|---|
| % packaging scrap | 115 | 13.6% | 13.5% | 13.4% | 13.4% | 13.4% | 13.4% | 13.4% | 13.4% | 13.4% | 13.4% |
| % packaging scrap | 380 | 12.7% | 12.7% | 12.6% | 12.6% | 12.6% | 12.6% | 12.6% | 12.6% | 12.6% | 12.6% |
| % packaging scrap | 950 | 12.5% | 12.4% | 12.4% | 12.4% | 12.4% | 12.4% | 12.4% | 12.4% | 12.4% | 12.4% |
| % packaging scrap | 1900 | 12.4% | 12.4% | 12.4% | 12.4% | 12.4% | 12.4% | 12.4% | 12.4% | 12.4% | 12.4% |
| total scrap | 38 | 51.7% | 49.1% | 52.7% | 57.8% | 63.6% | 69.6% | 75.8% | 82.2% | 88.6% | 95.0% |
| total scrap | 115 | 42.4% | 34.8% | 33.9% | 34.7% | 36.1% | 37.9% | 39.8% | 41.9% | 44.1% | 46.3% |
| total scrap | 380 | 37.5% | 27.7% | 24.9% | 24.0% | 23.7% | 23.8% | 24.0% | 24.4% | 24.9% | 25.5% |
| total scrap | 950 | 35.7% | 25.3% | 22.0% | 20.6% | 19.8% | 19.4% | 19.2% | 19.1% | 19.2% | 19.2% |
| total scrap | 1900 | 35.1% | 24.4% | 20.9% | 19.3% | 18.4% | 17.8% | 17.4% | 17.2% | 17.1% | 17.0% |

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method of optimizing self-supporting film production in the processing of a film dosage product comprising the steps of:
    (a) determining at least one scrap factor which relates to a total amount of scrap in processing a film dosage product;
    (b) correlating said at least one scrap factor to at least one processing parameter; and
    (c) adjusting the at least one processing parameter to reduce the total amount of scrap in processing said film dosage product:,
    wherein one or more of said steps is performed with a computer system; and
    wherein the total amount of scrap is defined by the formula:

$$T_S (m^2) = M_{LA} (m^2) + ([C_{SS} + S_{SS} + P_{SS}] * W_C) (m^2)$$

wherein
$T_S$ comprises one or more of $M_{LA}$, $C_{SS}$, $S_{SS}$, and $W_C$; and
$T_S$ is the total amount of scrap;
$M_{LA}$ is mixing losses area;
$C_{SS}$ is coating start/stop losses;
$S_{SS}$ is slitting start/stop loss;
$P_{SS}$ is packaging start/stop loss; and
$W_C$ is coating width.

2. The method of claim 1, wherein said scrap factor comprises a scrap for mixing factor.

3. The method of claim 2, wherein said scrap for mixing factor comprises scrap lost to hoses.

4. The method of claim 2, wherein said scrap for mixing factor comprises scrap lost due to the coating of the mixer.

5. The method of claim 1, wherein said scrap factor comprises a scrap for coating factor.

6. The method of claim 5, wherein said scrap for coating factor comprises scrap for start-up of the film forming process.

7. The method of claim 5, wherein said scrap for coating factor comprises scrap for shut-down of the film forming process.

8. The method of claim 5, wherein said scrap for coating factor comprises scrap for drying.

9. The method of claim 8, wherein said scrap for drying comprises scrap related to oven length.

10. The method of claim 1, wherein said scrap factor comprises a scrap for slitting factor.

11. The method of claim 1, wherein said scrap factor comprises a scrap for packaging factor.

12. The method of claim 1, further comprising the step of modifying a processing parameter that relates to a plurality of said scrap factors.

13. The method of claim 1, wherein the adjusting step further comprises adjusting a tank size of said film processing.

14. The method of claim 1, wherein the adjusting step further comprises adjusting a film sheet coating width.

15. The method of claim 1, wherein the adjusting step further comprises minimizing a hose length from a control volume of mixed material to a film sheet and construction area.

16. The method of claim 1, wherein the scrap that is reduced comprises start-up scrap.

17. The method of claim 1, wherein the scrap that is reduced comprises shut-down scrap.

18. The method of claim 1, wherein the adjusting step is completed in line.

19. A system for optimizing self-supporting film production in the processing of a film dosage product comprising:
    (a) a film manufacturing apparatus, comprising a mixer, a film former, and a cutting apparatus; and
    (b) a computer system for compiling and processing data related to the film manufacturing apparatus and at least one film dosage product characteristic;
    wherein the computer system is capable of controlling at least one processing parameter to reduce the total amount of scrap in processing said film dosage product and optimize the yield of said film dosage product;
    wherein the total amount of scrap is defined by the formula:

$$T_S (m^2) = M_{LA} (m^2) + ([C_{SS} + S_{SS} + P_{SS}] * W_C) (m^2)$$

wherein
$T_S$ comprises one or more of $M_{LA}$, $C_{SS}$, $S_{SS}$, $P_{SS}$, and $W_C$; and
$T_S$ is the total amount of scrap;
$M_{LA}$ is mixing losses area;
$C_{SS}$ is coating start/stop losses;
$S_{SS}$ is slitting start/stop loss;
$P_{SS}$ is packaging start/stop loss; and
$W_C$ is coating width.

20. The system of claim 19, wherein the system is capable of adjusting the processing parameters in real-time.

21. The system of claim 19, wherein the film manufacturing apparatus is remotely adjustable.

22. The method of claim 1, wherein the dosage product comprises a pharmaceutical active.

23. The system of claim 19, wherein the dosage product comprises a pharmaceutical active.

* * * * *